United States Patent
Caliskan et al.

(10) Patent No.: US 10,636,204 B2
(45) Date of Patent: *Apr. 28, 2020

(54) CORED ROCK ANALYSIS PLANNING THROUGH CT IMAGES

(71) Applicant: Saudi Arabian Oil Company, Dhahran (SA)

(72) Inventors: Sinan Caliskan, Dhahran (SA); Abdullah M. Shebatalhamd, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/598,756

(22) Filed: Oct. 10, 2019

(65) Prior Publication Data
US 2020/0051330 A1    Feb. 13, 2020

Related U.S. Application Data

(63) Continuation of application No. 15/718,333, filed on Sep. 28, 2017, which is a continuation of application
(Continued)

(51) Int. Cl.
*G01V 1/40* (2006.01)
*G06K 9/00* (2006.01)
(Continued)

(52) U.S. Cl.
CPC ............ *G06T 17/05* (2013.01); *E21B 25/00* (2013.01); *G01N 33/24* (2013.01); *G06T 7/00* (2013.01);
(Continued)

(58) Field of Classification Search
USPC ....... 382/100, 103, 106, 108–109, 128, 141, 382/154, 162, 168, 173, 181, 190, 199,
(Continued)

(56) References Cited

U.S. PATENT DOCUMENTS

| 3,373,440 A | 3/1968 | Jenkins et al. |
| 4,854,163 A | 8/1989 | Mount, II et al. |

(Continued)

FOREIGN PATENT DOCUMENTS

| CA | 2516872 A1 | 2/2007 |
| EP | 0574237 A2 | 12/1993 |
| GB | 2302736 A | 1/1997 |

OTHER PUBLICATIONS

Hunt, Patricia et al.; "Computed Tomography as a Core Analysis Tool: Applications, Instrument Evaluation, and Image Improvement Techniques" Journal of Petroleum Technology, Sep. 1998; pp. 1203-1210.
(Continued)

*Primary Examiner* — Seyed H Azarian
(74) *Attorney, Agent, or Firm* — Bracewell LLP; Constance G. Rhebergen; Brian H. Tompkins

(57) ABSTRACT

Embodiments of the disclosure include methods, machines, and non-transitory computer-readable medium having one or more computer programs stored therein to enhance core analysis planning for a plurality of core samples of subsurface material. Embodiments can include positioning electronic depictions of structure of encased core samples of subsurface material on a display and determining portions of each of the images as different planned sample types thereby to virtually mark each of the images. Planned sample types can include, for example, full diameter samples, special core analysis samples, conventional core analysis samples, and mechanical property samples. Embodiments further can include transforming physical properties of encased core samples of subsurface material into images responsive to one or more penetrative scans by use of one or more computerized tomography (CT) scanners.

15 Claims, 24 Drawing Sheets
(3 of 24 Drawing Sheet(s) Filed in Color)

Related U.S. Application Data

No. 15/139,818, filed on Apr. 27, 2016, now Pat. No. 9,842,431.

(60) Provisional application No. 62/186,937, filed on Jun. 30, 2015.

(51) Int. Cl.
    *G06T 17/05* (2011.01)
    *G01N 33/24* (2006.01)
    *E21B 25/00* (2006.01)
    *G06T 7/00* (2017.01)
    *G01N 23/083* (2018.01)

(52) U.S. Cl.
    CPC ........ *G01N 23/083* (2013.01); *G06T 2200/24* (2013.01); *G06T 2207/10081* (2013.01); *G06T 2207/20221* (2013.01); *G06T 2207/30181* (2013.01); *G06T 2207/30204* (2013.01)

(58) Field of Classification Search
    USPC ............ 382/203, 219, 232, 254, 174, 276, 382/285–294, 305, 312; 378/5; 702/6
    See application file for complete search history.

(56) References Cited

U.S. PATENT DOCUMENTS

| | | | |
|---|---|---|---|
| 4,982,086 A | | 1/1991 | Withjack |
| 5,058,425 A | | 10/1991 | Davis, Jr. et al. |
| 5,109,697 A | | 5/1992 | Millheim et al. |
| 6,275,563 B1 | | 8/2001 | Griffin, Jr. |
| 7,853,045 B2 * | 12/2010 | Touati ...................... G06K 9/00 382/109 |
| 8,200,465 B2 | | 6/2012 | Suarez-Rivera et al. |
| 9,127,529 B2 | | 9/2015 | Guzman et al. |
| 9,146,200 B2 | | 9/2015 | Zarra |
| 2007/0061079 A1 * | 3/2007 | Hu ........................... E21B 25/00 702/6 |
| 2014/0119497 A1 * | 5/2014 | Guzman ................. E21B 49/02 378/5 |
| 2015/0146936 A1 * | 5/2015 | Mezghani ............... G06T 5/006 382/109 |
| 2016/0187509 A1 * | 6/2016 | Boot ....................... G01V 1/30 382/109 |

OTHER PUBLICATIONS

International Search Report and Written Opinion for International Application No. PCT/US2016/039975 (SA5365/PCT); dated Sep. 16, 2016 (pp. 1-13).

Schlumberger, "Oilfield Glossary core analysis" available as of Feb. 23, 2015 at: http://www.glossary.oilfield.slb.com/En/Terms/c/core analysis.aspx; pp. 1.

Schlumberger, "Oilfield Glossary core plug" available as of Feb. 23, 2015 at: http://glossary.oilfield.slb.com/en/Terms/core_plug.aspx; pp. 1.

Schlumberger, "Oilfield Glossary core" available as of Feb. 21, 2015 at: http://www_glossary_oilfield.slb.com/en/Terms/core.aspx; pp. 1.

Schlumberger, "Oilfield Glossary gamma ray densitometer" available as of Feb. 20, 2015 at: http://www.glossary.oiilfield.slb.com/en/Terms/g/gamma_ray_densitometer .aspx; pp. 1.

Schlumberger, "Oilfield Glossary natural gamma ray spectroscopy" available as of Feb. 20, 2015 at: http://www.glossary.oilfield.slb.com/en/Terms/n/natural_gamma_ray_spectroscopy aspx; pp. 1.

Schlumberger, "Oilfield Glossary preserved core" available as of Feb. 21, 2015 at: http://www.glossary.oilfield.slb.com/en/Terms/p/preserved_core.aspx; pp. 1.

Schlumberger, "Oilfield Glossary routine core analysis" available as of Feb. 23, 2015 at: http://www.glossary.oilfield.slb.com/en/Terms/r/routine_core_ analysis.aspx; pp. 1.

Walls, Joel, et al. "Digital rock physics provide critical insights to characterize Eagle Ford." The American Oil&Gas Repórter (Feb. 28, 2011). pp. 1-4.

Wikipedia, "Gamma ray spectrometer" available as of Feb. 20, 2015 at: http://en.wikipedia.org/wiki/Gamma_ray_spectrometer; pp. 1-6.

Wikipedia, "Gamma spectroscopy" available as of Feb. 20, 2015 at: http://en.wikipedia.org/wiki/Gamma_spectroscopy; pp. 1-7.

* cited by examiner

104

| Whole Core Interval and Plugging Depth Selection | | | | | | | |
|---|---|---|---|---|---|---|---|
| | | | | Whole Core Interval | | | |
| Top Depth | Bottom Depth | Core Nr | Tube Nr | Top Depth | Bottom Depth | SCAL Plug Depth | CCA Plug Depth |
| 7201.0 | 7202.0 | 2 | 2 | 7201.1 | 7201.6 | 7201.8 | 7202.0 |
| 7202.0 | 7203.0 | 2 | 2 | 7202.0 | 7202.5 | | |
| 7203.0 | 7204.0 | 2 | 2 | 7203.0 | 7203.5 | 7203.7 | 7203.9 |
| 7204.0 | 7205.0 | 2 | 2 | 7204.2 | 7204.7 | | |
| 7205.0 | 7206.0 | 2 | 2 | 7205.0 | 7205.5 | 7205.7 | 7205.9 |
| 7206.0 | 7207.0 | 2 | 1 | | | | |
| 7207.0 | 7208.0 | 3 | 1 | | | | |
| 7208.0 | 7209.0 | 3 | 1 | | | | |
| 7209.0 | 7210.0 | 3 | 1 | | | | |
| 7210.0 | 7211.0 | 3 | Missing | | | | |
| 7211.0 | 7212.0 | 4 | 4 & 3 | | | | |
| 7212.0 | 7213.0 | 4 | 3 | | | | |
| 7213.0 | 7214.0 | 4 | 3 | 7213.0 | 7213.5 | 7213.9 | |
| 7214.0 | 7215.0 | 4 | 3 | | | 7214.7 | 7214.9 |
| 7215.0 | 7216.0 | 4 | 3 | 7215.0 | 7215.5 | 7215.7 | 7215.9 |
| 7216.0 | 7217.0 | 4 | 3 | 7216.0 | 7216.5 | | |
| 7217.0 | 7218.0 | 4 | 2 | 7217.0 | 7217.5 | 7217.7 | 7217.9 |
| 7218.0 | 7219.0 | 4 | 2 | 7218.0 | 7218.5 | 7218.7 | 7218.9 |
| 7219.0 | 7220.0 | 4 | 2 | 7219.1 | 7219.6 | 7219.9 | |
| 7220.0 | 7221.0 | 4 | 2 | 7220.0 | 7220.5 | 7220.7 | 7220.9 |
| 7221.0 | 7222.0 | 4 | 2 & 1 | 7221.0 | 7221.5 | | |
| 7222.0 | 7223.0 | 5 | Missing | | | | |
| 7223.0 | 7224.0 | 5 | Missing | | | | |
| 7224.0 | 7225.0 | 5 | Missing | | | | |
| 7225.0 | 7226.0 | 5 | 8 | | | | |
| 7226.0 | 7227.0 | 5 | 8 & 7 | | | 7226.7 | 7226.9 |
| 7227.0 | 7228.0 | 5 | 7 | 7227.2 | 7227.7 | | |
| 7228.0 | 7229.0 | 5 | 7 | 7228.0 | 7228.5 | 7228.7 | 7228.9 |

| Default or Modified | Comments |
|---|---|
| M | Fracture(s): 7201.1 & 7202.0 |
| D | Fracture(s): 7202.0 & 7202.7 |
| D | |
| M | Fracture(s): 7204.2 & 7204.8 |
| D | |
| M | Fracture(s): 7206.2 |
| M | RUBBLE |
| M | RUBBLE |
| M | RUBBLE |
| | |
| M | RUBBLE |
| M | RUBBLE & Fracture(s): 7212.3 & 7212.5 & 7212.7 & 7213.0 |
| M | Fracture(s): 7213.0 & 7213.7 |
| M | Fracture(s): 7214.4 |
| D | Fracture(s): 7215.5 |
| M | Fracture(s): 7216.5 |
| D | Fracture(s): 7217.0(s) & 7217.6(s) & 7218.0 |
| D | Fracture(s): 7218.0 & 7218.8 |
| M | Fracture(s): 7219.1(s) & 7219.8 & 7220.0 |
| D | Fracture(s): 7220.0 |
| D | |
| | |
| | |
| | |
| M | |
| M | |
| M | Fracture(s): 7227.2(s) & 7227.9 |
| D | Fracture(s): 7228.6 |

FIG. 7B

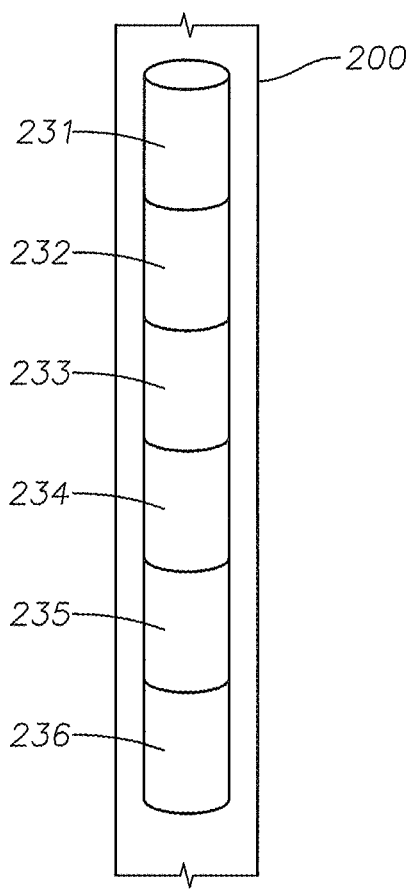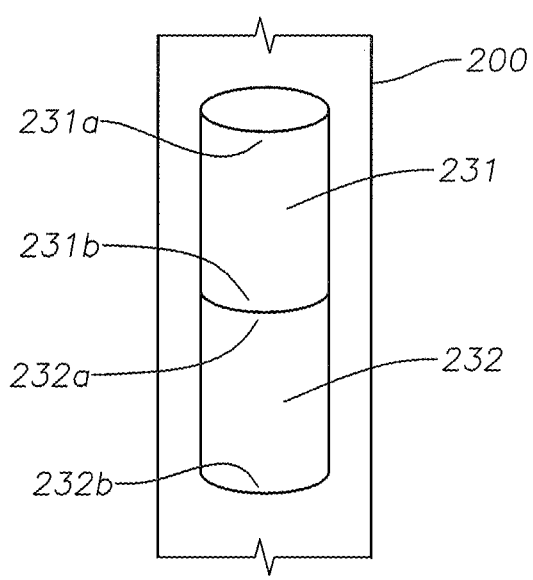
FIG. 10
FIG. 11

| Example dicom img files | | |
|---|---|---|
| Name | Type | Size |
| CT.1.2.392.200036.9116.2.5.1.16.1613467410.1359161718.456979 | 456979 File | 514 KB |
| CT.1.2.392.200036.9116.2.5.1.16.1613467410.1359161727.406129 | 406129 File | 514 KB |
| CT.1.2.392.200036.9116.2.5.1.16.1613467410.1359161736.353886 | 353886 File | 514 KB |
| CT.1.2.392.200036.9116.2.5.1.16.1613467410.1359161691.524370 | 524370 File | 514 KB |
| CT.1.2.392.200036.9116.2.5.1.16.1613467410.1359161700.531043 | 531043 File | 514 KB |
| CT.1.2.392.200036.9116.2.5.1.16.1613467410.1359161709.503650 | 503650 File | 514 KB |
| CT.1.2.392.200036.9116.2.5.1.16.1613467410.1359161673.514881 | 514881 File | 514 KB |
| CT.1.2.392.200036.9116.2.5.1.16.1613467410.1359161682.512065 | 512065 File | 514 KB |
| CT.1.2.392.200036.9116.2.5.1.16.1613467410.1359161646.631306 | 631306 File | 514 KB |

| Pilot tif images | | |
|---|---|---|
| Name | Type | Size |
| c01t01 | TIFF Image | 128 KB |
| c01t02 | TIFF Image | 157 KB |
| c01t03 | TIFF Image | 155 KB |
| c01t04 | TIFF Image | 156 KB |
| c01t05 | TIFF Image | 154 KB |
| c01t06 | TIFF Image | 156 KB |
| c01t07 | TIFF Image | 155 KB |
| c01t08 | TIFF Image | 142 KB |
| c01t09 | TIFF Image | 156 KB |
| c01t10 | TIFF Image | 157 KB |
| c01t11 | TIFF Image | 156 KB |

FIG. 19

CORED ROCK ANALYSIS PLANNING THROUGH CT IMAGES

CROSS-REFERENCE TO RELATED PATENT APPLICATIONS

This application is a continuation of and claims priority from U.S. application Ser. No. 15/718,333, filed Sep. 28, 2017, and titled "CORED ROCK ANALYSIS PLANNING THROUGH CT IMAGES," which is a continuation of and claims priority from U.S. application Ser. No. 15/139,818, filed Apr. 27, 2016, and titled "CORED ROCK ANALYSIS PLANNING THROUGH CT IMAGES," which claims priority from U.S. Provisional Application No. 62/186,937, filed Jun. 30, 2015, and titled "CORED ROCK ANALYSIS PLANNING THROUGH CT IMAGES," each of which are incorporated by reference in their entirety for purposes of United States patent practice.

BACKGROUND

Field of the Disclosure

Embodiments of the disclosure relate to hydrocarbon reservoir production and, more specifically, to methods, machines, and non-transitory computer-readable medium having computer program stored therein to enhance core sample analysis planning.

Description of the Related Art

During rock coring in development and exploration of a hydrocarbon reservoir to produce hydrocarbons, such as oil and gas, rock core samples of subsurface material are collected. The process of obtaining these samples, called cores or core samples, produces a corebore hole that is formed into and defined by and traverses the subsurface (that is, the rock or other material beneath the surface). A core sample is the extracted subsurface material (such as rock or stone) from the subsurface through the newly formed corebore. In some instances, core samples can be taken from and compose a portion of a reservoir or formation. A corebore is typically vertical or slightly deviated as it extends from the surface into the subsurface. In some circumstances, however, a core sample may be extracted from a highly deviated, substantially horizontal, or even inverted horizontal (inclining) corebore or wellbore. Following extraction, cores may be stored in protective containers, transported to a laboratory or other location, and analyzed to evaluate characteristics of the hydrocarbon reservoir or subsurface. For example, as illustrated in FIG. 1 (Prior Art), whole core samples may be cored (that is, extracted from a corebore) at step 401. The samples may be cut and placed in tubes at step 402 then transported to a core laboratory at step 403. For instance, the cores may be transported in groups of tubes 421. The process of coring whole core samples at step 401 to transporting the samples to a core laboratory at step 403 make take one week to several months, for instance. Upon arrival at a core laboratory, cores may be put in a queue at step 404, and further analysis may wait until the cores are taken out of their core barrels and laid on a table for viewing and marking 405. Analysis then may include gamma ray measurement at step 406. The cores then may be opened for taking 360 degree images at step 407 and displaying on the table at step 408. Further, the cores may be selected and marked at step 409, as will be understood by those skilled in the art. Core analysis planning may include determining which core samples to use for further testing, including identifying core samples from which to take plugs or other samples and determining the location of such plugs or other samples within the identified core samples. The process of analysis from putting the cores in the queue at step 404 to selecting and marking the cores at step 409 may take two weeks to several months, for example. Then, sampling and testing may begin, including coring (that is, taking samples from) the core samples at step 410 to produce plugs 422 and performing conventional core analysis at step 411, special core analysis at step 412, rock mechanics at step 413, and other tests at step 414, as will be understood by those skilled in the art. The plugs 422 then may be stored in containers 423.

SUMMARY

Core analysis planning, however, often may be prepared with only a limited amount of available information about the actual core samples. That is, the actual state of the cores (such as the level of fractures or rubble sections in the cores) may not yet be known. Since the actual state of the cores may not yet be known when core analysis planning decisions are made, estimations of plug or whole core rock samples (that is, the type, quantity, and location of plugs or other test samples, for instance) may not be accurate and may result in confusing expectations. For example, fractures and rubble sections in a core may restrict the type, quantity, and location of plugs or other test samples that may be taken from such a core. Such fractures and rubble sections may not be identifiable until the core is taken out of its protective barrel, cleaned, and examined on a viewing table. These limitations may produce an inaccurate estimation of the number of testing samples that may be taken. Therefore, final, accurate planning or any required adjustments may be made only after the opening of the rock samples on the table, as will be understood by those skilled in the art, where the rock core samples may be examined and locations of the plug samples may be marked. This method may be quite a lengthy process and may require supporting techniques to enhance accuracy as well as speed in the decision-making stage.

Applicant has recognized that, in existing types of core analysis planning, the actual state of the cores may not yet be known and that this limited knowledge impairs the effectiveness of core analysis planning. Advantageously, embodiments of the disclosure can enable an advanced core analysis planning by forming an image of the state of the cores using computerized tomography (CT) scanning images while the cores are still in their protective core barrels and integrating these CT images into the planning process. In addition to integrating the CT scanning images into the core analysis planning process, embodiments of the disclosure advantageously can provide virtual marking of sample locations. Embodiments thus advantageously can enable enhanced speed and accuracy in core sample planning analysis. Further, embodiments of the disclosure can simulate positions of planned testing samples, such as plugs or full diameter samples, on the core samples depicted in the CT scanning images. Embodiments of the disclosure thus advantageously can include a special purpose simulator machine, for example.

Embodiments of the disclosure can include methods, machines, and non-transitory computer-readable medium having one or more computer programs stored therein to enhance core analysis planning for core samples of subsurface material. For example, a method according to an embodiment can include positioning a plurality of electronic, two-dimensional, substantially rectangular depictions of structure of one or more real, three-dimensional, substantially cylindrical core samples of subsurface material in a substantially side-by-side arrangement on a display. Each of the one or more core samples can have a first end and a second end. Further, the second end of each of the one or more core samples can be associated with an original location within a corebore downhole relative to an original location within the corebore of the first end of the respective one of the one or more core samples. Additionally, each core sample can be encased in a substantially cylindrical container thereby to define an encased core, and the plurality of depictions of structure of the one or more encased cores thereby can define a plurality of pilot images. Each of the plurality of pilot images can have a first end of the pilot image, which can be associated with the first end of the respective core sample depicted in the respective pilot image. Each of the plurality of pilot images also can have a second end of the pilot image, which can be associated with the second end of the respective core sample depicted in the respective pilot image. Further, the respective first end of each of the pilot images can be aligned along an imaginary line substantially near an upper end of an electronic user interface. A method according to an embodiment also can include determining each of one or more portions of each of the plurality of pilot images as one of a plurality of planned sample types thereby to virtually mark each of the plurality of pilot images.

In some instances, the one or more core samples can be a plurality of core samples. Furthermore, the plurality of core samples can have a sequential order associated with original locations by downhole position of the plurality of core samples within the corebore. For example, the first end of each of the plurality of core samples—other than the first core sample in the sequential order—can be associated with an original location within the corebore downhole relative to an original location within the corebore of the second end of the respective prior core sample in the sequential order. In addition, the plurality of pilot images can be arranged in an order on the electronic user interface thereby to define a display order. A position within the display order can be associated with the position within the sequential order of the plurality of core samples of the respective core sample depicted in the respective pilot image, for example. In addition, the display order can be one of the following: from a left side to a right side of the electronic user interface, from the right side to the left side of the electronic interface, from the upper end to a lower end of the electronic user interface, and from the lower end to the upper end of the electronic user interface. Further, a method also can include superimposing a geometric shape on each of the one or more portions of each of the plurality of pilot images responsive to the virtual mark of the plurality of pilot images, in some circumstances. Each of the plurality of planned sample types can have a predetermined geometric shape associated therewith. Additionally, the respective geometric shape associated with each of the plurality of planned sample types can be depicted as a different color. The plurality of planned sample types can include, for example, a full diameter sample, a special core analysis (SCAL) sample, a conventional core analysis (CCA) sample, and a mechanical property sample. Further, determining each of the one or more portions of each of the plurality of pilot images as one of the plurality of planned sample types can include simulating a respective position of a planned testing sample on the respective core sample depicted in the respective pilot image. A method further can include displaying (1) measurements of depth of the original locations of the plurality of core samples within the corebore and (2) measurements of depth of the original locations of the portions of each of the plurality of core samples associated with each of the one or more virtually marked portions of each of the plurality of pilot images.

Additionally, in some circumstances, each of the one or more substantially cylindrical containers can be a protective barrier made of one or more of a plurality of materials that are at least partially transparent to electromagnetic energy, and the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). Further, a method also can include transforming physical properties of the one or more encased cores into the plurality of pilot images responsive to one or more penetrative scans of each of the one or more protective barriers by use of one or more computerized tomography (CT) scanners.

Embodiments of the disclosure also can include machines to enhance core analysis planning for core samples of subsurface material. For example, a machine according to an embodiment can include one or more processors and one or more displays in communication with the one or more processors. The one or more displays also can be configured to display an electronic user interface thereon. The electronic user interface can have an upper end, a lower end, a left side, and a right side. A machine according to an embodiment also can include non-transitory memory medium in communication with the one or more processors. The memory medium can include computer-readable instructions stored therein that when executed cause the one or more processors to perform a series of operations. For example, the operations can include positioning a plurality of electronic, two-dimensional, substantially rectangular depictions of structure of one or more real, three-dimensional, substantially cylindrical core samples of subsurface material in a substantially side-by-side arrangement on one or more of the one or more displays. Each of the one or more core samples can have a first end and a second end. The second end of each of the one or more core samples, for example, can be associated with an original location within a corebore downhole relative to an original location within the corebore of the first end of the respective one of the one or more core samples. Further, each core sample can be encased in a substantially cylindrical container thereby to define an encased core, and the plurality of depictions of structure of the one or more encased cores thereby can define a plurality of pilot images. Each of the plurality of pilot images can have a first end of the pilot image that can be associated with the first end of the respective core sample depicted in the respective pilot image. Additionally, each of the plurality of pilot images can have a second end of the pilot image that can be associated with the second end of the respective core sample depicted in the respective pilot image. The respective first end of each of the pilot images can be aligned along an imaginary line substantially near the upper end of the electronic user interface. Further, the operations can include determining each of one or more portions of each of the plurality of pilot images as one of a plurality of planned sample types thereby to virtually mark each of the plurality of pilot images.

In some instances, the one or more core samples can be a plurality of core samples. Further, the plurality of core samples can have a sequential order associated with original locations by downhole position of the plurality of core samples within the corebore. For example, the first end of each of the plurality of core samples—other than the first core sample in the sequential order—can be associated with an original location within the corebore downhole relative to an original location within the corebore of the second end of the respective prior core sample in the sequential order. Further, the plurality of pilot images can be arranged in an order on the electronic user interface thereby to define a display order. A position within the display order can be associated with the position within the sequential order of the plurality of core samples of the respective core sample depicted in the respective pilot image. In addition, the display order can be one of the following: from the left side to the right side of the electronic user interface, from the right side to the left side of the electronic interface, from the upper end to the lower end of the electronic user interface, and from the lower end to the upper end of the electronic user interface. The operations further can include superimposing, on the electronic user interface, a geometric shape on each of the one or more portions of each of the plurality of pilot images responsive to the virtual mark of the plurality of pilot images, for example. Each of the plurality of planned sample types can have a predetermined geometric shape associated therewith. Further, the respective geometric shape associated with each of the plurality of planned sample types can be depicted as a different color. For example, the plurality of planned sample types can include a full diameter sample, a special core analysis (SCAL) sample, a conventional core analysis (CCA) sample, and a mechanical property sample. In some instances, determining each of the one or more portions of each of the plurality of pilot images as one of the plurality of planned sample types can include simulating a respective position of a planned testing sample on the respective core sample depicted in the respective pilot image. The operations further can include displaying, by use of the electronic user interface, measurements of depth of the original locations of the plurality of core samples within the corebore and measurements of depth of the original locations of the portions of each of the plurality of core samples associated with each of the one or more virtually marked portions of each of the plurality of pilot images.

Further, in some circumstances, each of the one or more substantially cylindrical containers can be a protective barrier made of one or more of a plurality of materials that are at least partially transparent to electromagnetic energy, and the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). A machine further can include one or more computerized tomography (CT) scanners in communication with the one or more processors. The one or more CT scanners also can be configured to scan the one or more encased cores. In addition, the operations further can include transforming physical properties of the one or more encased cores into the plurality of pilot images responsive to one or more penetrative scans of each of the one or more protective barriers by use of the one or more CT scanners.

Embodiments of the disclosure further can include non-transitory computer-readable medium having one or more computer programs stored therein operable by one or more processors to enhance core analysis planning for core samples of subsurface material. For example, in non-transitory computer-readable medium having one or more computer programs stored therein operable by one or more processors according to an embodiment, the one or more computer programs can include a set of instructions that, when executed by the one or more processors, cause the one or more processors to perform a series of operations. The operations can include, for example, positioning a plurality of electronic, two-dimensional, substantially rectangular depictions of structure of one or more real, three-dimensional, substantially cylindrical core samples of subsurface material in a substantially side-by-side arrangement on a display. Each of the one or more core samples can have a first end and a second end. For example, the second end of each of the one or more core samples can be associated with an original location within a corebore downhole relative to an original location within the corebore of the first end of the respective one of the one or more core samples. Further, each core sample can be encased in a substantially cylindrical container thereby to define an encased core, and the plurality of depictions of structure of the one or more encased cores thereby can define a plurality of pilot images. Each of the plurality of pilot images can have a first end of the pilot image, which can be associated with the first end of the respective core sample depicted in the respective pilot image. Each of the plurality of pilot images also can have a second end of the pilot image, which can be associated with the second end of the respective core sample depicted in the respective pilot image. Further, the respective first end of each of the pilot images can be aligned along an imaginary line substantially near an upper end of an electronic user interface. The operations also can include determining each of one or more portions of each of the plurality of pilot images as one of a plurality of planned sample types thereby to virtually mark each of the plurality of pilot images.

In some instances, the one or more core samples can be a plurality of core samples. Further, the plurality of core samples can have a sequential order associated with original locations by downhole position of the plurality of core samples within the corebore. For example, the first end of each of the plurality of core samples—other than the first core sample in the sequential order—can be associated with an original location within the corebore downhole relative to an original location within the corebore of the second end of the respective prior core sample in the sequential order. Further, the plurality of pilot images can be arranged in an order on the electronic user interface thereby to define a display order, and a position within the display order can be associated with the position within the sequential order of the plurality of core samples of the respective core sample depicted in the respective pilot image. In addition, the display order can be one of the following: from a left side to a right side of the electronic user interface, from the right side to the left side of the electronic interface, from the upper end to a lower end of the electronic user interface, and from the lower end to the upper end of the electronic user interface. In some circumstances, the operations further can include superimposing a geometric shape on each of the one or more portions of each of the plurality of pilot images responsive to the virtual mark of the plurality of pilot images. For example, each of the plurality of planned sample types can have a predetermined geometric shape associated therewith, and the respective geometric shape associated with each of the plurality of planned sample types can be depicted as a different color. Further, the plurality of planned sample types can include a full diameter sample, a special core analysis (SCAL) sample, a conventional core analysis (CCA) sample, and a mechanical property sample. In some instances, determining each of the one or more portions of each of the plurality of pilot images as one of the plurality of planned sample types can include simulating a respective position of a planned testing sample on the respective core sample depicted in the respective pilot image. The operations still further can include displaying measurements of depth of the original locations of the plurality of core samples within the corebore and measurements of depth of the original locations of the portions of each of the plurality of core samples associated with each of the one or more virtually marked portions of each of the plurality of pilot images.

In some circumstances, each of the one or more substantially cylindrical containers can be a protective barrier made of one or more of a plurality of materials that are at least partially transparent to electromagnetic energy, and the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). Additionally, the operations further can include transforming physical properties of the one or more encased cores into the plurality of pilot images responsive to one or more penetrative scans of each of the one or more protective barriers by use of one or more computerized tomography (CT) scanners.

Embodiments of the disclosure thus can provide advanced core analysis planning, for example, including integration of CT scanning images and image processing within core analysis planning to increase the speed and accuracy of core analysis planning. The integration of CT scanning images into the core analysis planning process can obtain enhanced efficiency, cost and time saving, and enhanced accuracy in the core analysis planning process. Advantageously, enhanced speed and accuracy in turn can affect positively the end result: core analysis data. Further, embodiments of the disclosure can be used as a non-destructive and non-invasive tool in core analysis planning through which faster and more accurate decisions can be made. After completion of processes according to embodiments of the disclosure, for example, rock cores can be kept entirely as received without any disturbance to the preservation methods within the original core barrels. Application of embodiments of the disclosure in the core analysis planning practice thus can provide positive impacts and significant contributions. Still further, embodiments of the disclosure can provide significant monetary savings to an entity that performs core analysis planning through efficiency, enhanced speed, and accuracy of core analysis data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

FIG. 7A is a schematic diagram of an electronic user interface according to an embodiment of the disclosure.

FIG. 7B is a schematic diagram of an electronic user interface according to an embodiment of the disclosure.

FIG. 10 is a schematic diagram of a corebore and core samples according to an embodiment of the disclosure.

FIG. 11 is a schematic diagram of a corebore and core samples according to an embodiment of the disclosure.

FIG. 18 is a schematic diagram of an electronic user interface according to an embodiment of the disclosure.

FIG. 19 is a schematic diagram of an electronic user interface according to an embodiment of the disclosure.

DETAILED DESCRIPTION

So that the manner in which the features and advantages of the embodiments of methods, machines, systems, and non-transitory computer-readable medium having computer program stored therein of the present disclosure, as well as others, which will become apparent, may be understood in more detail, a more particular description of the embodiments of methods, machines, systems, and non-transitory computer-readable medium having computer program stored therein of the present disclosure briefly summarized supra may be had by reference to the embodiments thereof, which are illustrated in the appended drawings, which form a part of this specification. It is to be noted, however, that the drawings illustrate only various embodiments of the embodiments of methods, machines, systems, and non-transitory computer-readable medium having computer program stored therein of the present disclosure and are therefore not to be considered limiting of the embodiments of methods, machines, systems, and non-transitory computer-readable medium having computer program stored therein of the present disclosure's scope as it may include other effective embodiments as well.

As part of a core analysis procedure, throughout the coring stages (that is, before, during, and after the coring), core analysis planning meetings can be carried out to establish the test methods that are likely to achieve the best possible rock data. At this stage, since the core samples are usually still within the core barrels, these discussions can occur without any visual support for this planning. Even if all the discussions are completed and test methods are agreed, the marking of sample locations typically is postponed until the core samples are taken out of their protective core barrels, cleaned, and laid on a viewing table, which can require a period of waiting time that can be months.

Figure 5:
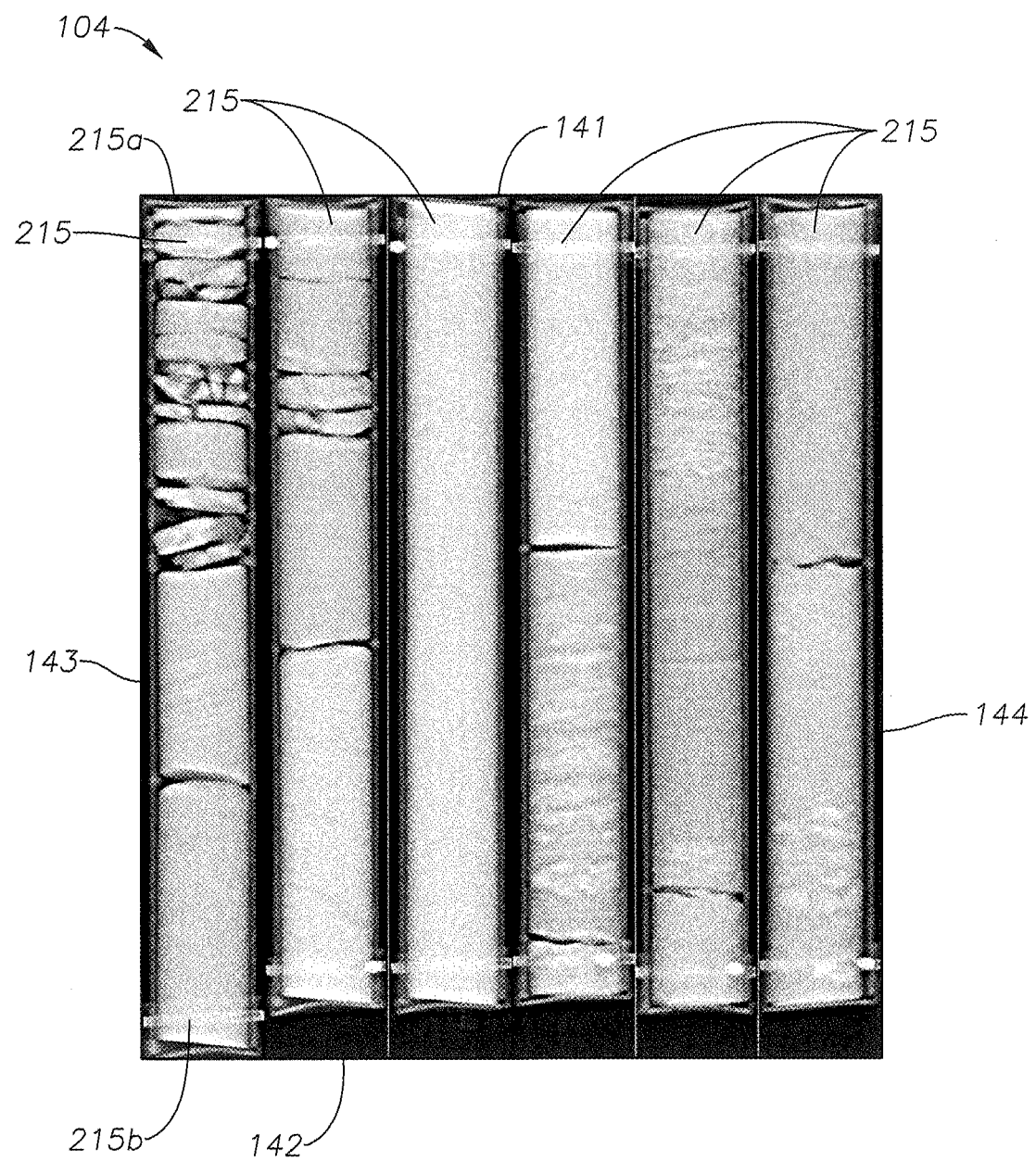
FIG. 5 is a schematic diagram of an electronic user interface according to an embodiment of the disclosure.
Figure 6:
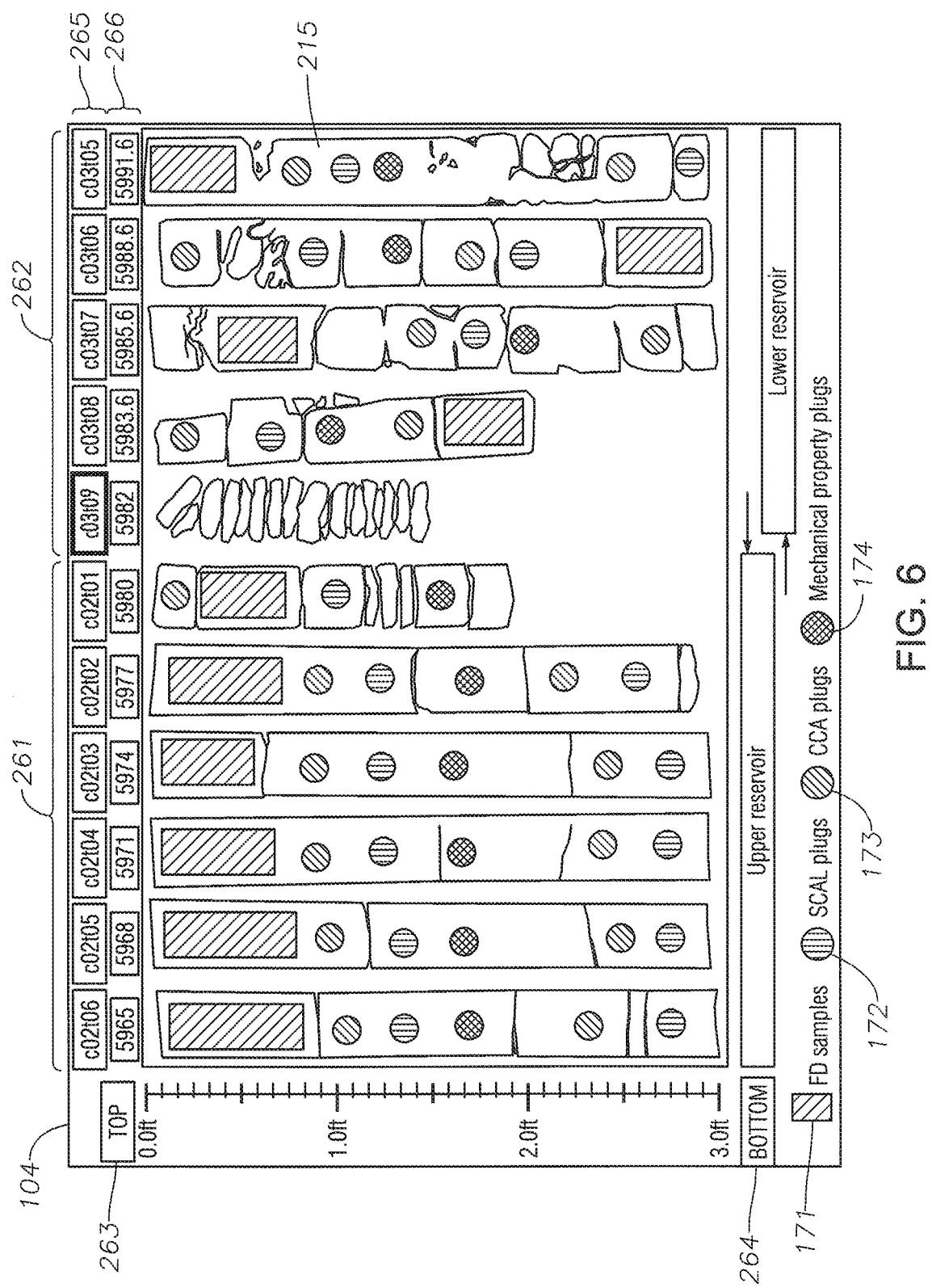
FIG. 6 is a schematic diagram of an electronic user interface according to an embodiment of the disclosure.
Figure 9:
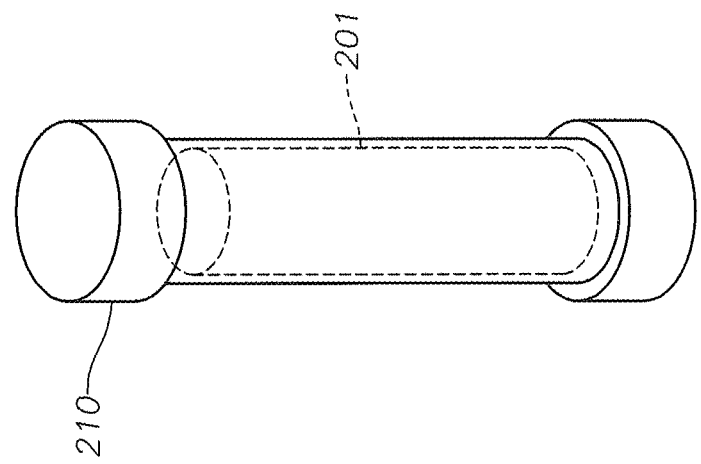
FIG. 9 is a schematic diagram of a core sample and container according to an embodiment of the disclosure.
Figure 25:
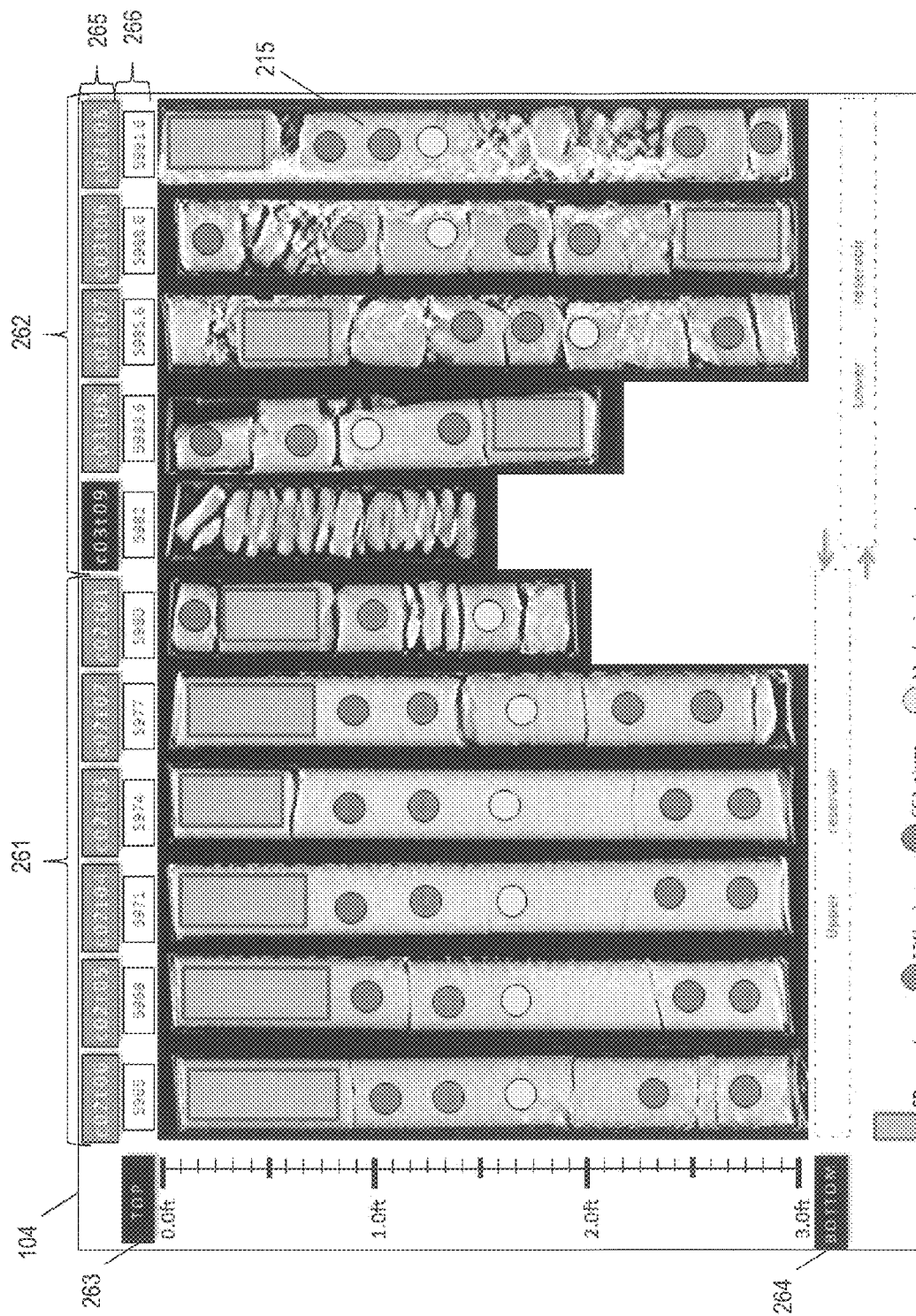
FIG. 25 is a schematic diagram of an electronic user interface according to an embodiment of the disclosure.

Embodiments of the disclosure advantageously can include methods, machines, and non-transitory computer-readable medium having one or more computer programs stored therein to enhance core analysis planning for core samples of subsurface material. For example, a method to enhance core analysis planning for core samples of subsurface material according to an embodiment can include positioning a plurality of electronic, two-dimensional, substantially rectangular depictions 215 of structure of one or more real, three-dimensional, substantially cylindrical core samples 201 of subsurface material in a substantially side-by-side arrangement on a display, such as by use of an electronic user interface 104, as illustrated in FIG. 5, FIG. 6, and FIG. 25, for example. An electronic user interface 104 can be displayed using a stand-alone computer program, for example, or using word processing, spreadsheet, or presentation software, for instance. Each of the one or more core samples 201 can have a first end 202 and a second end 203, as illustrated in FIG. 9, for example. Further, the second end 203 of each of the one or more core samples 201 can be associated with an original location within a corebore 200 downhole relative to an original location within the corebore 200 of the first end 202 of the respective one of the one or more core samples 201. For example, the second end 203 of each of the one or more core samples 201 can be associated with a deeper original location within the corebore 200 than the first end 202. That is, the core sample 201 can have been oriented in a vertical corebore 200 such that the first end 202 was nearer to the surface than the second end 203. For example, as illustrated in FIG. 11, the second end 231b of core sample 231 is depicted at a deeper original location within the corebore 200 than the first end 231a of core sample 231. Additionally, the second end 232b of core sample 232 is depicted at a deeper original location within the corebore 200 than the first end 232a of core sample 232. Although the corebore 200 is depicted as a vertical corebore in FIG. 11, for example, the corebore 200 also can be a directional corebore, such as a horizontal core. For instance, the corebore 200 can be an inverted horizontal corebore; in such an inverted horizontal corebore, the second end 203 of a core sample 201 can be nearer to the surface than the first end 203 in terms of true vertical depth but nevertheless downhole relative to the first end 203 within the corebore.

Figure 8:
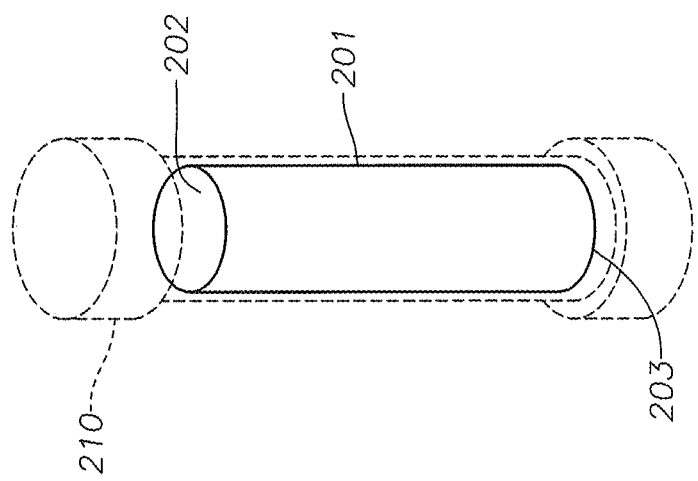
FIG. 8 is a schematic diagram of a core sample and container according to an embodiment of the disclosure.
Figure 12:
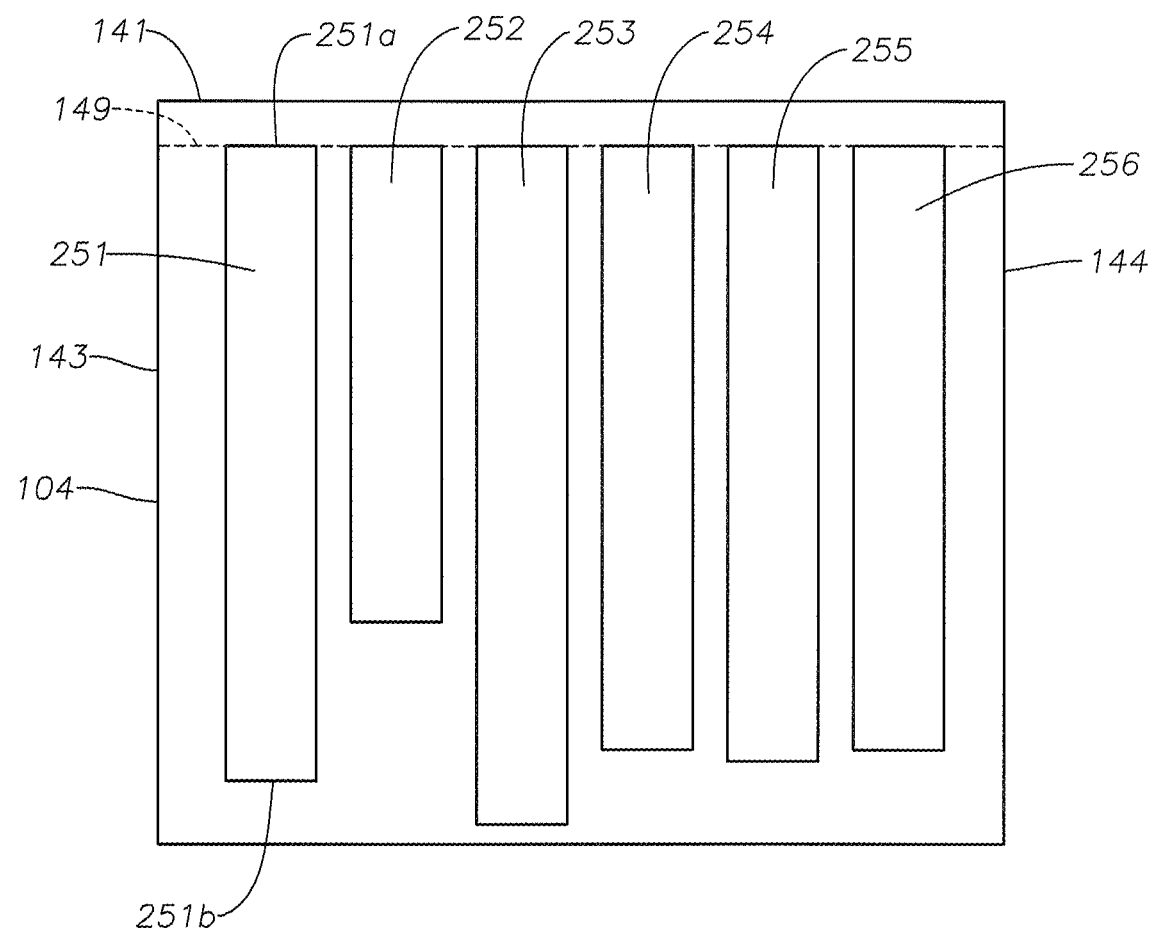
FIG. 12 is a schematic diagram of an electronic user interface according to an embodiment of the disclosure.

Additionally, each core sample 201 can be encased in a substantially cylindrical container 210 thereby to define an encased core. That is, an encased core can be a core sample 201 encased in a substantially cylindrical container 210, as illustrated in FIG. 8 and FIG. 9, for example. Further, in some instances, each of the one or more substantially cylindrical containers 210 can be a protective barrier made of one or more of a plurality of materials that are at least partially transparent to electromagnetic energy. For example, the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). The one or more substantially cylindrical containers 210 also can be any other non-metallic container, for example. In some instances, the one or more substantially cylindrical containers 210 can be non-visually opaque, such as containers 210 that are made of aluminum, PVC, cardboard, PE, PP, carbon fiber, or fiberglass. In other instances, the one or more substantially cylindrical containers 210 can be visually opaque, such as containers 210 that are made of PE, PP, polycarbonates, or PMMA. Regardless of whether the containers 210 are visually opaque, the one or more substantially cylindrical containers 210 can be transparent to the type of energy transmitted by, for instance, computerized tomography (CT) scanners 102. For example, X-rays can be a good measure of the frequency permissiveness of the containers 210. Additionally, the plurality of depictions 215 of structure of the one or more encased cores thereby can define a plurality of pilot images 215. That is, a pilot image 215 can depict both a core sample 201 and its respective container 210. Each of the plurality of pilot images 215 can have a first end 215a of the pilot image 215 that is associated with the first end 202 of the respective core sample 201 depicted in the respective pilot image 215, as illustrated in FIG. 5, for example. Each of the plurality of pilot images 215 also can have a second end 215b of the pilot image 215 that is associated with the second end 203 of the respective core sample 201 depicted in the respective pilot image 215. For example, pilot image 251, as depicted in FIG. 12, can depict core sample 231, as illustrated in FIG. 11. Pilot image 251 can have a first end 251a and a second end 251b, as illustrated in FIG. 12, for instance. Further, first end 251a of pilot image 251 can be associated with first end 231a of core sample 231, and second end 251b of pilot image 251 can be associated with second end 231b of core sample 231. As positioned, according to an embodiment of the disclosure, the respective first end 215a of each of the pilot images 215 can be aligned along an imaginary line 149 substantially near an upper end 141 of an electronic user interface 104, as illustrated in FIG. 12, for example. A method according to an embodiment also can include determining each of one or more portions of each of the plurality of pilot images 215 as one of a plurality of planned sample types thereby to virtually mark each of the plurality of pilot images 215. That is, a method can include virtually marking each of the plurality of pilot images 215 to indicate a plan to take a plug or other sample from the core sample 201 depicted in the respective pilot image 215.

In some instances, the one or more core samples 201 can be a plurality of core samples 201, and the plurality of core samples 201 can have a sequential order associated with original locations by downhole position of the plurality of core samples 201 within the corebore 200, as illustrated in FIG. 10, for example. As depicted, for example, core samples 201 illustrated in the original locations within the corebore 200 can include, in order of increasing depth: core sample 231, core sample 232, core sample 233, core sample 234, core sample 235, and core sample 236. That is, the sequential order of the core samples 201 illustrated in FIG. 10 is: core sample 231, core sample 232, core sample 233, core sample 234, core sample 235, and core sample 236. In addition, the first end 202 of each of the plurality of core samples 201—other than the first core sample in the sequential order—can be associated with an original location within the corebore 200 downhole relative to an original location within the corebore of the second end 203 of the respective prior core sample in the sequential order. For example, in the case of a vertical corebore 200, deeper core samples 201 can be later in the sequential order. (The sequential order as described does not have a core sample prior to the first core sample in the sequential order.) For example, when core sample 232 has a deeper original location within the corebore 200 than core sample 231, as illustrated in FIG. 10 and FIG. 11, for example, core sample 231 precedes core sample 232 in the sequential order, and the first end 232a of core sample 232 has a deeper original location within the corebore 200 than the second end 231b of core sample 231, as illustrated in FIG. 11, for instance.

Additionally, the plurality of pilot images 215 can be arranged in an order on the electronic user interface 104 thereby to define a display order. Further, the display order can be one of the following: from a left side 143 to a right side 144 of the electronic user interface 104, from the right side 144 to the left side 143 of the electronic interface 104, from the upper end 141 to a lower end 142 of the electronic user interface 104, and from the lower end 142 to the upper end 141 of the electronic user interface 104. For example, an example display order from a left side 143 to a right side 144 of the electronic user interface 104 is illustrated, for instance, in FIG. 12. That is, the example display order depicted in FIG. 12, for example, is: pilot image 251, pilot image 252, pilot image 253, pilot image 254, pilot image 255, and pilot image 256. In addition, a position within the display order can be associated with the position within the sequential order of the plurality of core samples 201 of the respective core sample 201 depicted in the respective pilot image 215, for example. For example, as depicted in FIG. 12, pilot image 251 can depict core sample 231, pilot image 252 can depict core sample 232, pilot image 253 can depict core sample 233, pilot image 254 can depict core sample 234, pilot image 255 can depict core sample 235, and pilot image 256 can depict core sample 236. Consequently, the position of a pilot image 215 in the display order can mirror the position of the respective depicted core sample 201 in the sequential order.

In some circumstances, a method further can include superimposing a geometric shape on each of the one or more portions of each of the plurality of pilot images 215 responsive to the virtual mark of the plurality of pilot images 215, as illustrated in FIG. 6 and FIG. 25, for example. More specifically, each of the plurality of planned sample types can have a predetermined geometric shape associated with the respective planned sample type. As depicted in FIG. 6 and FIG. 25, for example, geometric shapes can include rectangles and circles. Further, the respective geometric shape associated with each of the plurality of planned sample types can be depicted as a different color, as illustrated in FIG. 25, for example. In other instances, each planned sample type can be depicted in the same color, but each planned sample type can be associated with a different respective geometric shape. Further, in some circumstances, each planned sample type can be associated with the same geometric shape while color can vary by planned sample type. In addition, the plurality of planned sample types can include a full diameter sample, a special core analysis (SCAL) sample, a conventional core analysis (CCA) sample, and a mechanical property sample. For example, as illustrated in FIG. 6 and FIG. 25, rectangle 171 can indicate that a portion of a pilot image 215 is a planned full diameter sample. Likewise, circle 172 can indicate that a portion of a pilot image 215 is a planned SCAL sample, and circle 173 can indicate that a portion of a pilot image 215 is a planned CCA sample. Further, circle 174 can indicate that a portion of a pilot image 215 is a planned mechanical property sample. In some instances, rectangle 171 can be green, circle 172 can be blue, circle 173 can be red, and circle 174 can be yellow, for example, as illustrated in FIG. 25. Displaying and superimposing such geometric shapes advantageously can enable ready analysis of the planned sample types within a core sample 201 depicted in a pilot image 215. An individual pilot image 215 can be virtually marked with all, some, or none of the plurality of planned sample types. For example, in some instances, some tests cannot be performed due to the material presented. Further, in some circumstances, determining each of the one or more portions of each of the plurality of pilot images 215 as one of the plurality of planned sample types can include simulating a respective position of a planned testing sample on the respective core sample 201 depicted in the respective pilot image 215, as illustrated in FIG. 6 and FIG. 25, for example. For instance, a planned testing sample can include a planned full diameter sample, a planned SCAL plug, a planned CCA plug, and a planned mechanical property plug. As depicted in FIG. 6 and FIG. 25, for example, some of the pilot images 215 can be associated with an upper reservoir 261, and some of the pilot images 215 can be associated with a lower reservoir 262. Further, the length of the core samples 201 depicted in the pilot images 215 can be represented, for example, on a scale from zero to three feet, measured from top 263 to bottom 264 (that is, beginning at the first end 215a of a pilot image 215). For each pilot image 215, an indication of core and tube numbers 265 and depth 266 associated with the first end 215a of the respective pilot image 215 can be displayed.

Additionally, in some instances, a method further can include displaying (1) measurements of depth of the original locations of the plurality of core samples 201 within the corebore 200 and (2) measurements of depth of the original locations of the portions of each of the plurality of core samples 201 associated with each of the one or more virtually marked portions of each of the plurality of pilot images 215, as illustrated in FIG. 7A and FIG. 7B, for example, by use of electronic user interface 104. As depicted, for example, each row of a table can correspond to a core sample 201. For each core sample 201, the table can provide the top depth of the core sample 201 (that is, corresponding to the first end 202 of the respective core sample 201) and the bottom depth of the core sample 201 (that is, corresponding to the second end 203 of the respective core sample 201). The table further can identify a core number and a tube number. Still further, the table can identify any interval of depths over which the respective core sample 201 is whole (that is, top depth and bottom depth of whole core interval, as illustrated in FIG. 7A and FIG. 7B). The table still further can identify the location (by depth) of different planned sample types, such as, for example, planned SCAL samples and planned CCA samples. In addition, the table can identify status (for example, default or modified) and include any comments (for example, presence and location of fractures or rubble within the respective core sample 201). An embodiment of the disclosure thus advantageously can report all core samples 201 based on the pilot images 215 as part of core analysis planning.

Figure 14:
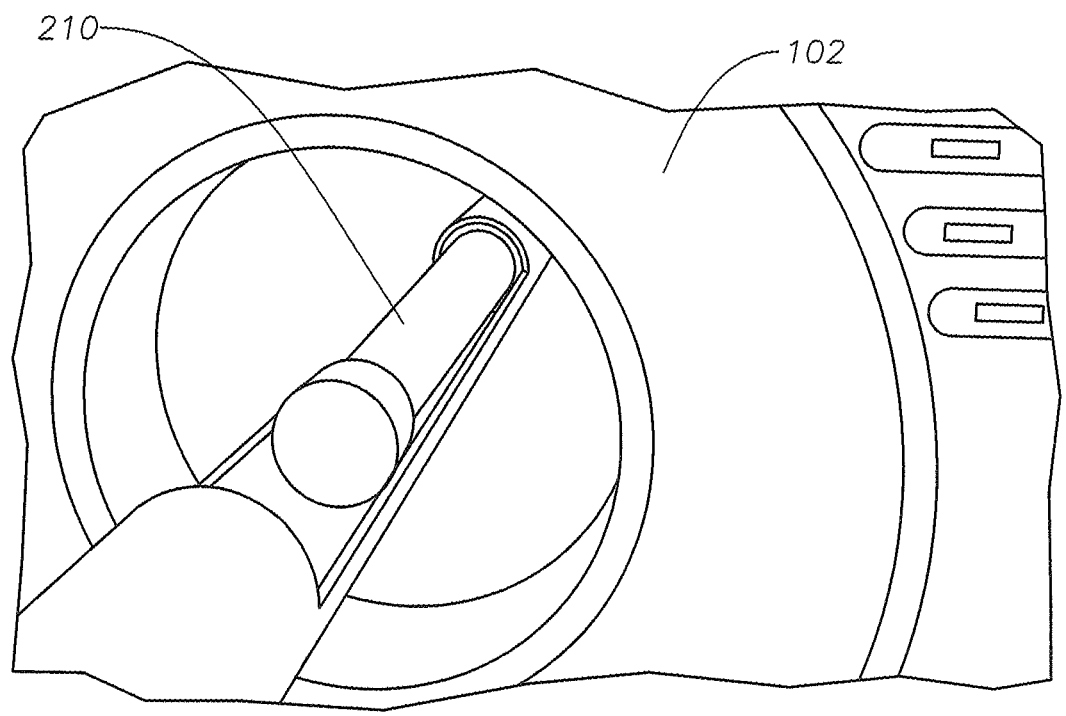
FIG. 14 is a schematic diagram of a CT scanner according to an embodiment of the disclosure.

Further, in some circumstances, a method further can include transforming physical properties of the one or more encased cores into the plurality of pilot images 215 responsive to one or more penetrative scans of each of the one or more protective barriers by use of one or more computerized tomography (CT) scanners 102. An example CT scanner 102 is illustrated in FIG. 14, for example. In an example configuration, a CT scanner 102 can scan a core sample 201 encased in a container 210 as the respective container 210 is conveyed through the CT scanner 102, as illustrated in FIG. 14, for example, and as will be understood by those skilled in the art. A container 210 can be three to five feet in length and can be capped and sealed at both ends to preserve the state of the core sample 201 within the container 210. Containers 210 thus can enable easy handling of core samples 201 and can protect the core samples 201 from disintegration and unnatural fractures.

Embodiments of the disclosure thus can provide a number of advantages. For example, a maximum number of testing samples that possibly can be obtained from a well can be accurately determined. This information can help engineers to optimize the number of tests, as well as the number of samples for each test type, before the actual core samples 201 are taken out of their protective core barrels 210. Additionally, after the core samples 201 are taken out of their protective core barrels 210, cleaned, and laid on the table, as will be understood by those skilled in the art, the predetermination of planned testing sample locations can make the physical marking of testing sample locations for sample extraction much easier.

Figure 3:
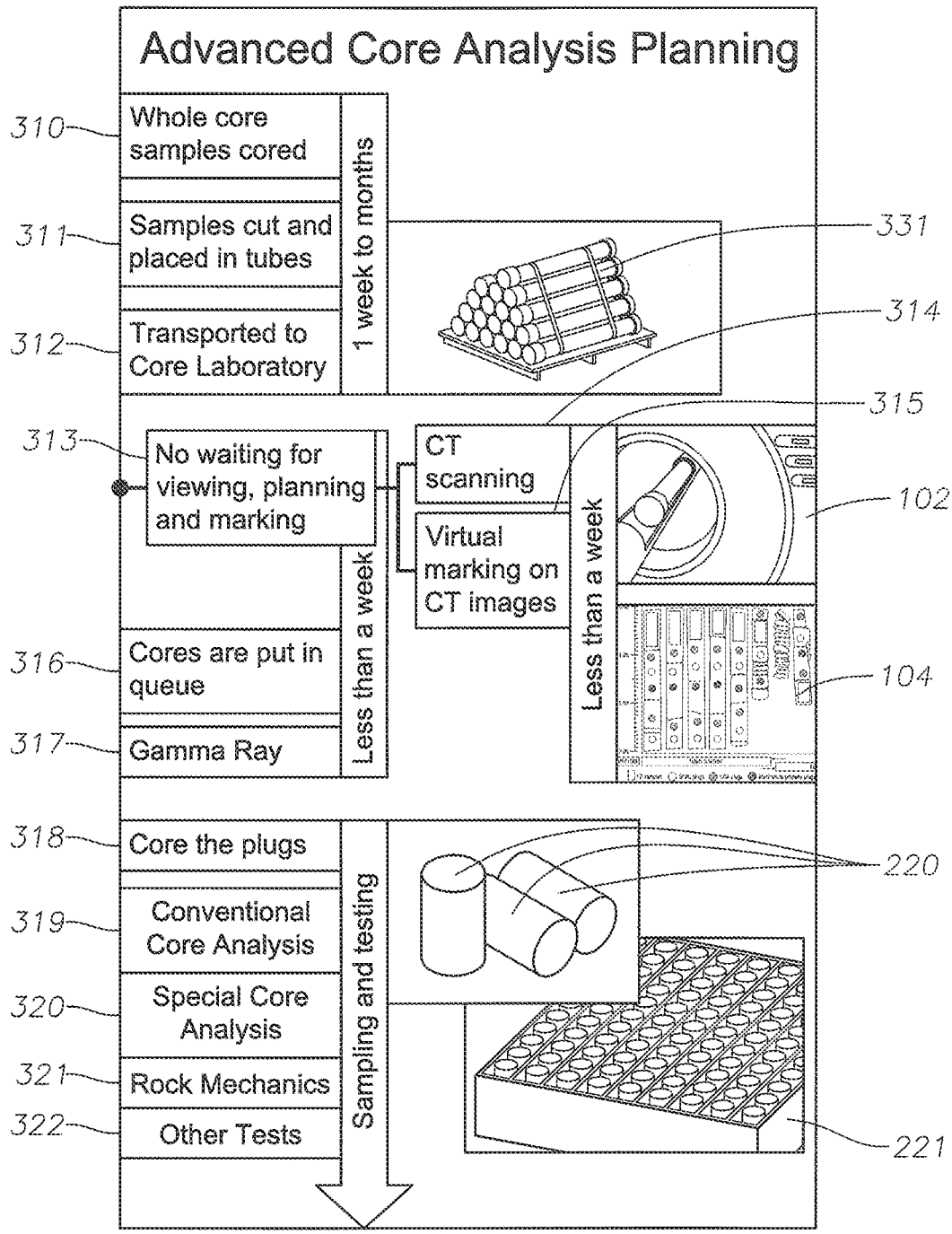
FIG. 3 is a schematic diagram of a method according to an embodiment of the disclosure.
Figure 15:
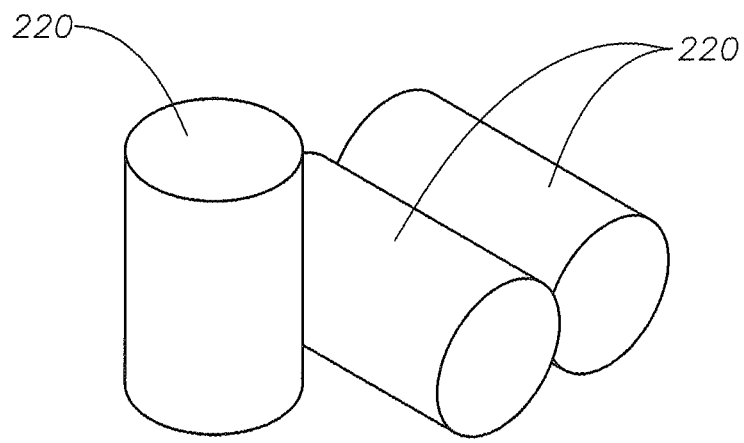
FIG. 15 is a schematic diagram of core sample plugs according to an embodiment of the disclosure.
Figure 16:
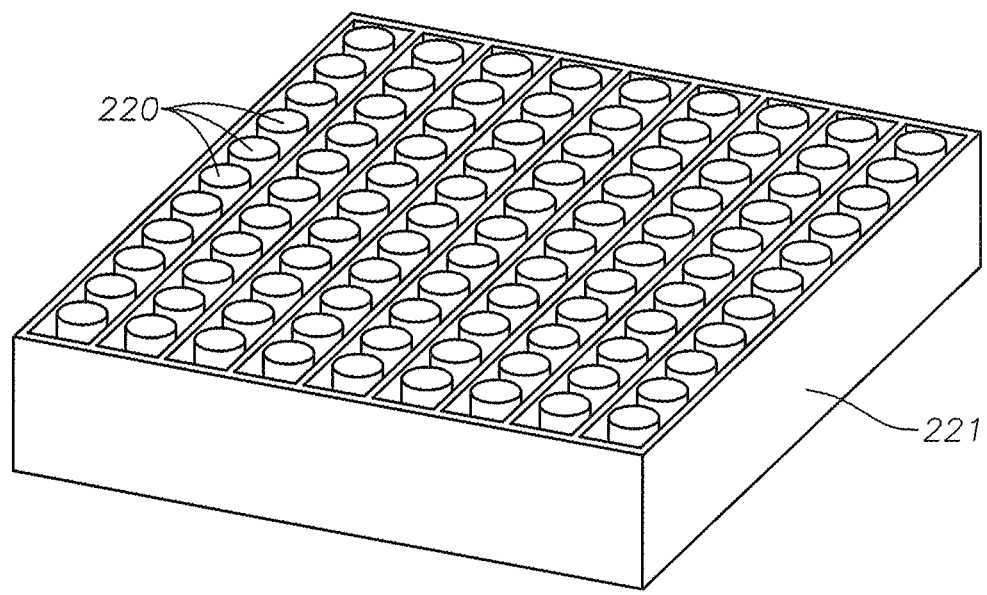
FIG. 16 is a schematic diagram of core sample plugs according to an embodiment of the disclosure.

For example, a method of core analysis according to one or more embodiments of the disclosure can be illustrated in FIG. 3, for example. As depicted, for example, whole core samples 201 can be cored (that is, extracted or removed from a corebore 200) at step 310, as will be understood by those skilled in the art. The core samples 201 can be cut and placed in tubes 210 at step 311 then transported to a core laboratory at step 312, for example, in groups of encased core samples on pallets 331. These initial steps, from extracting the whole core samples 201 from the corebore 200 at step 310 to transporting the core samples 201 to a core laboratory at step 312 can take one week to several months, for example. Upon arrival at a core laboratory, for example, embodiments of the disclosure advantageously can eliminate any wait for viewing, marking, and planning 313. For instance, embodiments can include CT scanning (by use of a CT scanner 102, for example) at step 314 and performing virtual marking on the CT images (for example, as depicted on an electronic user interface 104) at step 315, which can take less than a week. Cores 201 then can be put in a queue at step 316, and gamma ray detection can be performed at step 317, which can take less than a week. In some instances, 360 degree images of the cores 201 can be taken, as well. Sampling and testing then can begin, including coring the core samples 201 (that is, taking one or more test samples from the core samples 201) at step 318 to produce core plugs 220, as will be understood by those skilled in the art and as illustrated, for example, in FIG. 15. Sampling and testing also can include performing conventional core analysis at step 319, special core analysis at step 320, rock mechanics at step 321, and other tests at step 322, as will be understood by those skilled in the art. The core plugs 220 then can be labeled and stored, for example, in containers 221, as illustrated in FIG. 16, for example. The illustrated core analysis process thus can include integration of CT scanning images 215 (which also can be known as pilot images 215) into the planning process.

Figure 4:
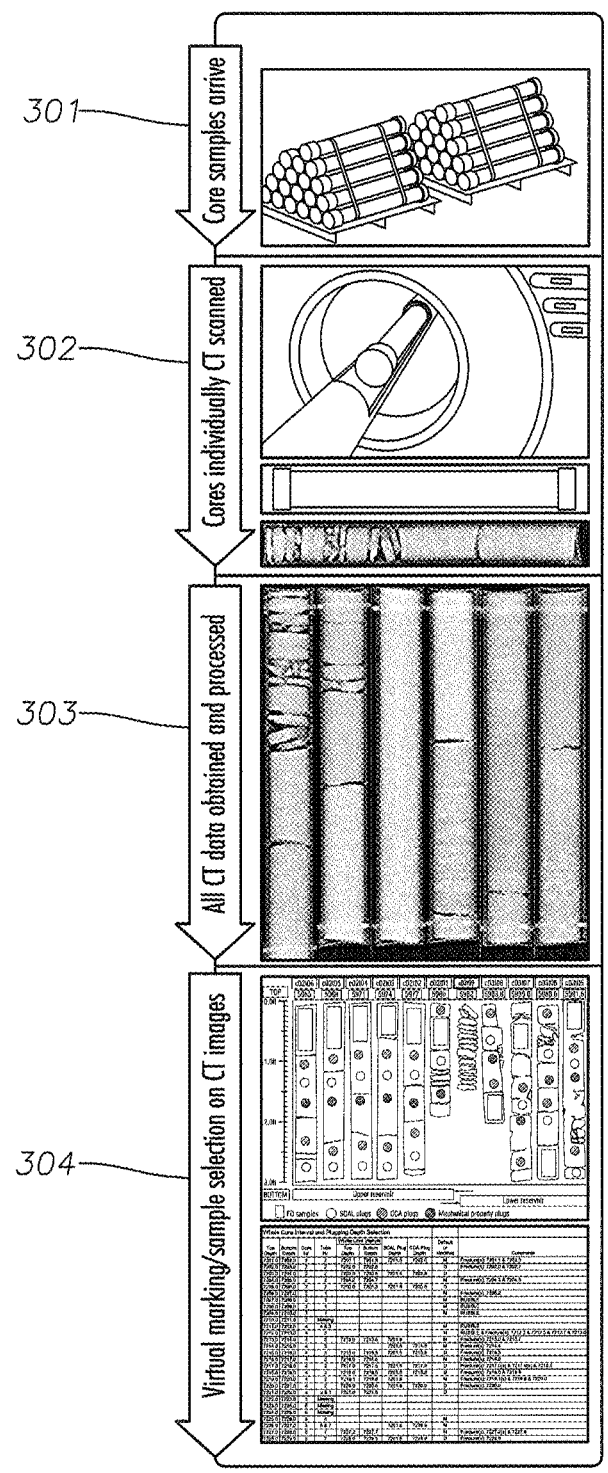
FIG. 4 is a schematic diagram of a method according to an embodiment of the disclosure.

CT scanning of whole cores 201 can include a carefully designed step-by-step workflow. For example, as illustrated in FIG. 4, a workflow according to an embodiment can include sequential steps involved in obtaining CT images 215 for an advanced core analysis planning. For example, steps can include, after core samples 201 arrive at step 301, individually CT scanning core samples 201 at step 302. Steps then can include obtaining and processing the CT scanning images 215 at step 303, which also can be known as pilot images 215, sometimes called pilot scan images, as illustrated, for instance, in FIG. 5. The pilot images 215, which can be digital radiographs (for example, similar to X-ray plates) of each core sample 201, can provide valuable information about the integrity of a core sample 201 without compromising its preserved state. That is, a core sample 201 can remain intact without changing the natural orientation of the rock or any pieces in the tube 210 through cleaning or other processes. Further, techniques according to embodiments of the disclosure can protect a core sample 201 from artificial damage or fractures, such as any damage that results from transportation or from being dropped while carried. Advantageously, embodiments of the disclosure thus can avoid destroying the core samples 201, which are preserved in the state in which they came out of the corebore 200, within their protective barrels 210 (that is, in reservoir condition) until they are opened, cleaned, cored, or sliced, for example. Pilot images 215 can provide an excellent opportunity to visualize—non-destructively—the cores 201 inside the core barrels 210 (for example, made of opaque material, such as aluminum, fiberglass, or PVC tubes) and can enable observation without compromising their storage condition and integrity. These images 215 can be organized such that consecutive tubes 210 are side by side and relevant technical data, for example, core and tube numbers (from smaller depth towards deeper depth value), are presented, as illustrated in FIG. 6 and FIG. 25, for example. Furthermore, their top and bottom positions can be aligned, that is, such that the top position is at the top and the bottom position is at the bottom, which can obviate the need for any further alignment. As depicted in FIG. 5, for instance, the changes of the gray tones within the pilot images 215 can indicate changes in density and, hence, the existence of a level of heterogeneity or changes in rock type. The thick, cross-sectional, straight, and, in some cases, irregular lines disturbing the continuity of a pilot image 215 can indicate the existence of fractures and breakages. The dark gray areas can indicate lower density, while the slightly light gray and brighter areas can indicate higher densities, which can help to identify rock facies.

After finalizing the orientation of the pilot images 215 as described supra, a core analysis process according to an embodiment of the disclosure can include virtual marking and sample selection on CT images 215 at step 304. For example, each test type can be designated with a certain color code, for example, full diameter (FD) samples in a green color, special core analysis (SCAL) samples (for example, plugs 220) in a blue color, conventional core analysis (CCA) samples (for example, plugs 220) in a red color, and rock mechanics (RM) samples (for example, plugs 220) in a yellow color. By using these color codes, all the required samples (including, for example, plugs 220) at the targeted depth can be marked, for example, as illustrated in FIG. 6 and FIG. 25, for example. During the virtual marking, excessively fractured and rubble areas can be avoided, which eventually can reveal the maximum possible samples (including, for example, plugs 220) that can be obtained from these cores 201. A detailed reporting of all the plug samples 220 also can be prepared based on the CT images 215, for example, as illustrated in FIG. 7A and FIG. 7B, which can strengthen further a core analysis process according to an embodiment of the disclosure. A CT scanning technique according to embodiments of the disclosure advantageously can contribute significantly to core analysis planning, particularly during the decision-making stage by speeding up the process and increasing the accuracy of the accumulated number of samples (including, for example, plugs 220) and their locations.

Figure 17:
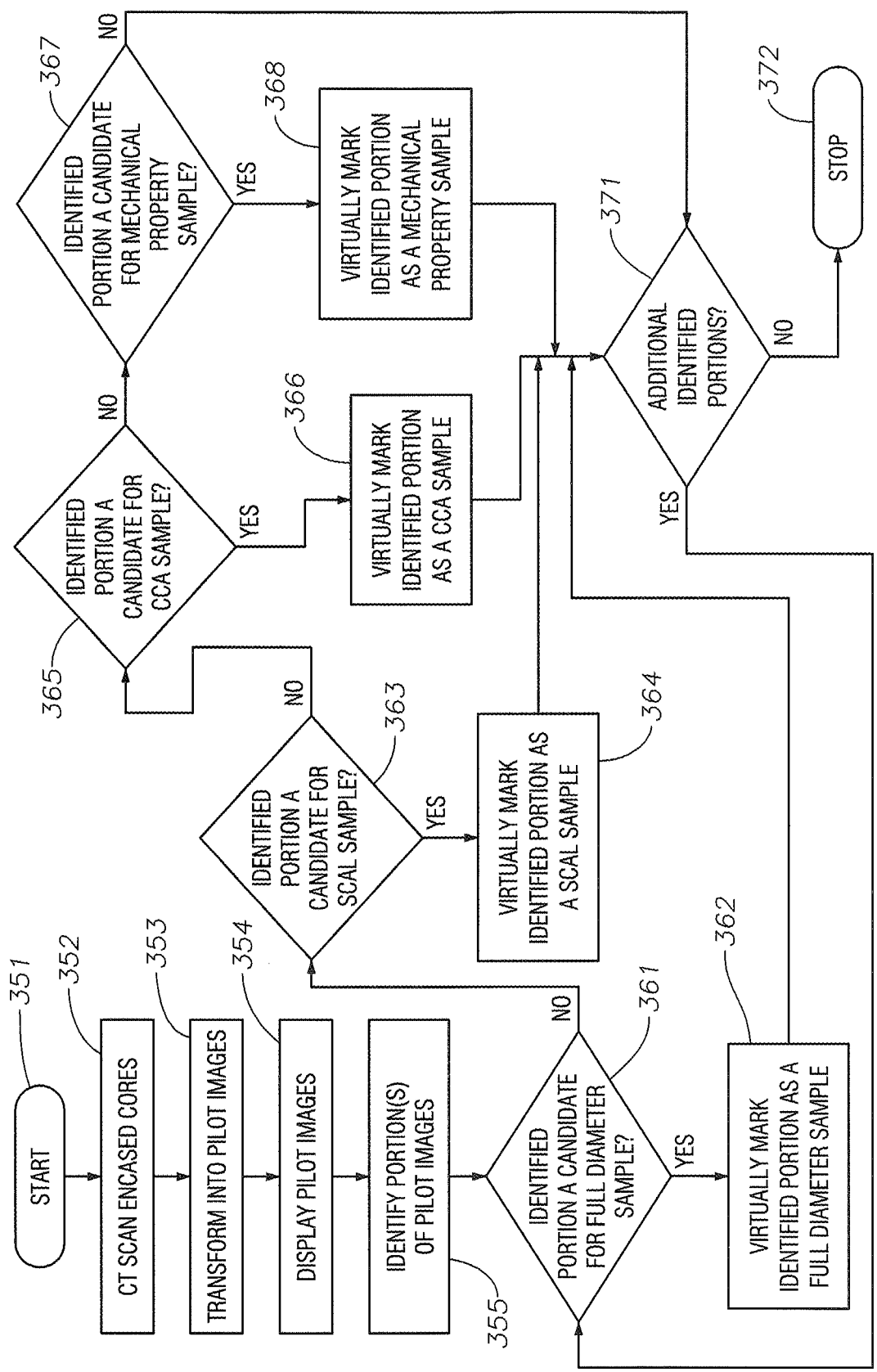
FIG. 17 is a schematic diagram of a method according to an embodiment of the disclosure.

Further, an example method is illustrated in FIG. 17, for instance. The method as depicted can start at step 351. Then, at step 352, encased cores can be CT scanned, and physical characteristics of the encased cores thus can be transformed into pilot images 215 at step 353. At step 354, pilot images 215 can be displayed, and one or more portions of the pilot images 215 can be identified as candidates for one of the planned sample types at step 355. The example method then can include determining—for a first portion of the identified one or more portions of the pilot images 215—whether the identified portion of the pilot images 215 indicates an area in the core sample 201 depicted in the respective pilot image 215 that is a candidate for a full diameter sample at step 361. If so, the method can include virtually marking the identified portion as a planned full diameter sample at step 362. If the identified portion is not such at a candidate (that is, step 361 is answered in the negative), the method can include determining whether the identified portion of a pilot image 215 indicates an area in the core sample 201 depicted in the respective pilot image 215 that is a candidate for a SCAL sample at step 363. If so, the method can include virtually marking the identified portion as a planned SCAL sample at step 364. If the identified portion is not such at a candidate (that is, step 363 is answered in the negative), the method can include determining whether the identified portion of a pilot image 215 indicates an area in the core sample 201 depicted in the respective pilot image 215 that is a candidate for a CCA sample at step 365. If so, the method can include virtually marking the identified portion as a planned CCA sample at step 366. If the identified portion is not such at a candidate (that is, step 365 is answered in the negative), the method can include determining whether the identified portion of a pilot image 215 indicates an area in the core sample 201 depicted in the respective pilot image 215 that is a candidate for a mechanical property sample at step 367. If so, the method can include virtually marking the identified portion as a planned mechanical property sample at step 368. If the identified portion is not such at a candidate (that is, step 367 is answered in the negative), the method can include determining whether additional identified portions of the pilot images 215 exist at step 371. If so, the method can include determining whether the next identified portion of the pilot images 215 indicates an area in the core sample depicted in the respective pilot image 215 that is a candidate for a SCAL sample at step 363. The method also can include determining whether additional identified portions of the pilot images 215 exist at step 371 after marking a portion at any of steps 362, 364, 366, and 368. If no additional identified portions of the pilot images 215 exist at step 371, the method can stop at step 372. Consequently, the method can include determining whether each identified portion of the one or more identified portions of the pilot images 215 indicates an area in the core sample depicted in the respective pilot image 215 that is a candidate for a full diameter sample (at step 361), a SCAL sample (at step 363), a CCA sample (at step 365), or a mechanical property sample (at step 367). That is, each identified portion of the pilot images 215 can be analyzed separately. The method thus permits any or all virtual markings to be used for a set of pilot images 215. That is, operation of the depicted method can cause the set of pilot images 215 to include one or more portions that are virtually marked as each of a full diameter sample, a SCAL sample, a CCA sample, and a mechanical property sample. Alternatively, operation of the method can cause the set of pilot images 215 to include only portions that are virtually marked with a single one of the sample types. Moreover, operation of the method can result in a set of pilot images 215 without any virtually marked sample types. Additionally, a single pilot image 215 can be virtually marked with all, none, or a combination of the sample types.

Figure 20:
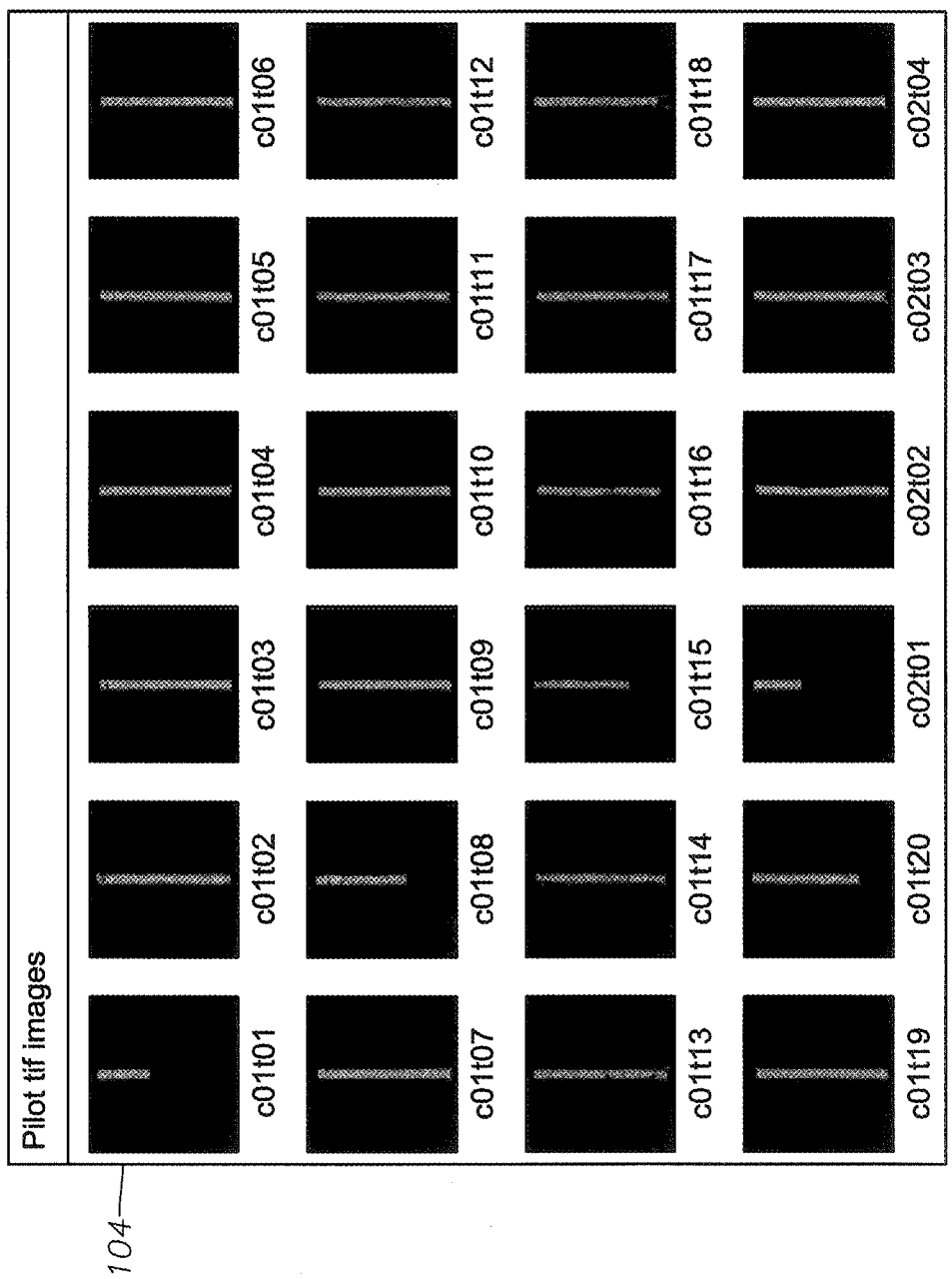
FIG. 20 is a schematic diagram of an electronic user interface according to an embodiment of the disclosure.
Figure 21:
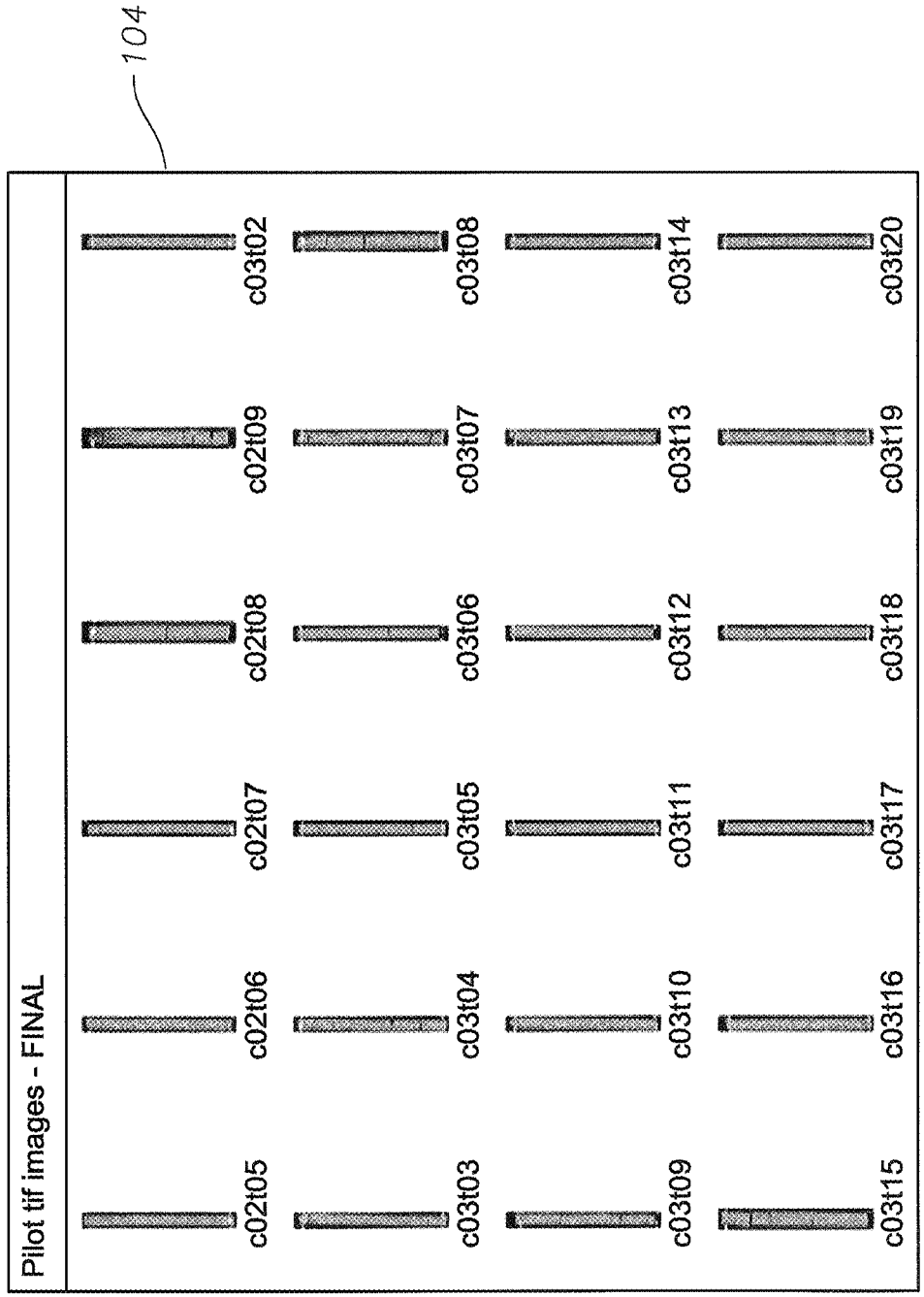
FIG. 21 is a schematic diagram of an electronic user interface according to an embodiment of the disclosure.
Figure 22:
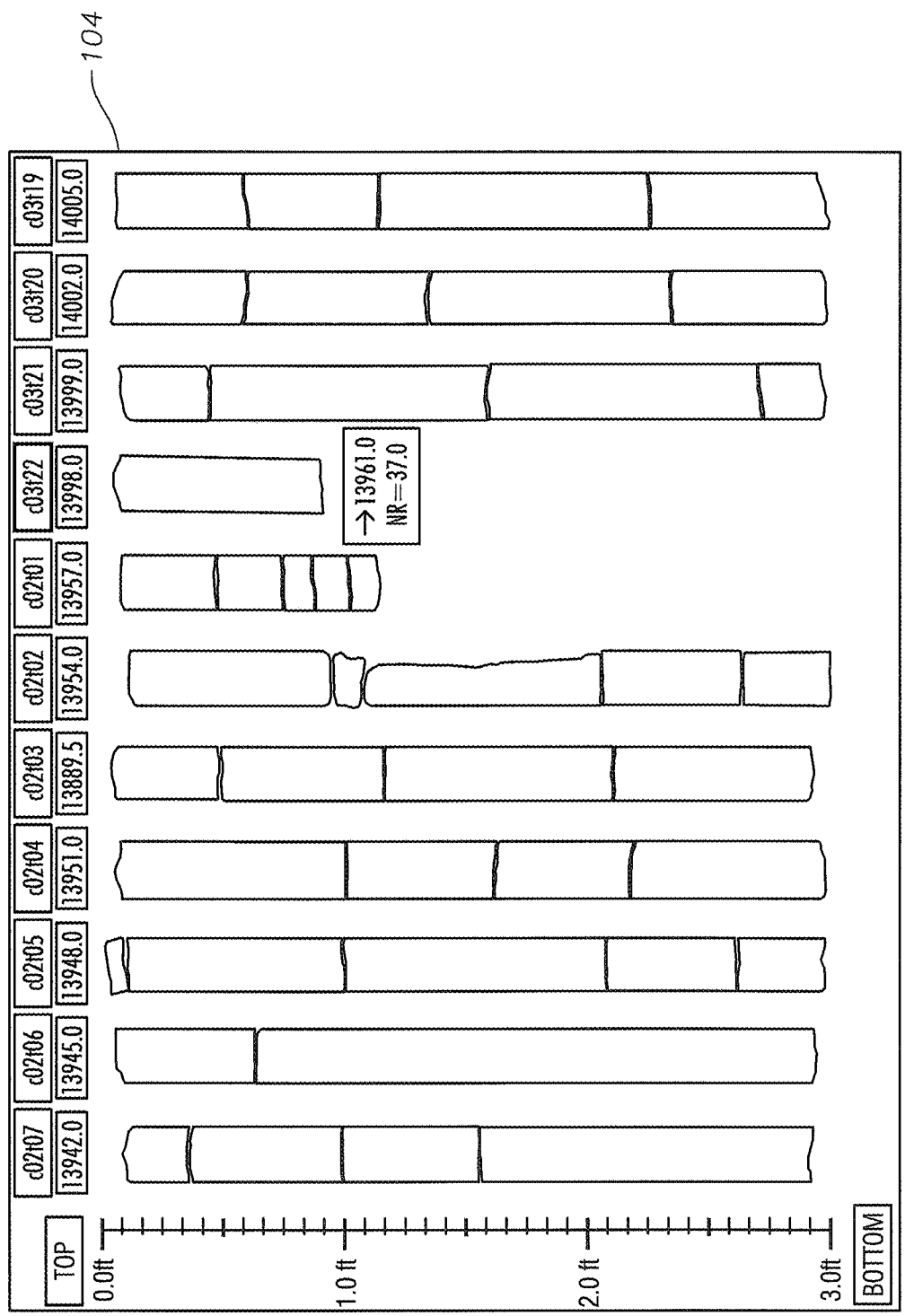
FIG. 22 is a schematic diagram of an electronic user interface according to an embodiment of the disclosure.
Figure 23:
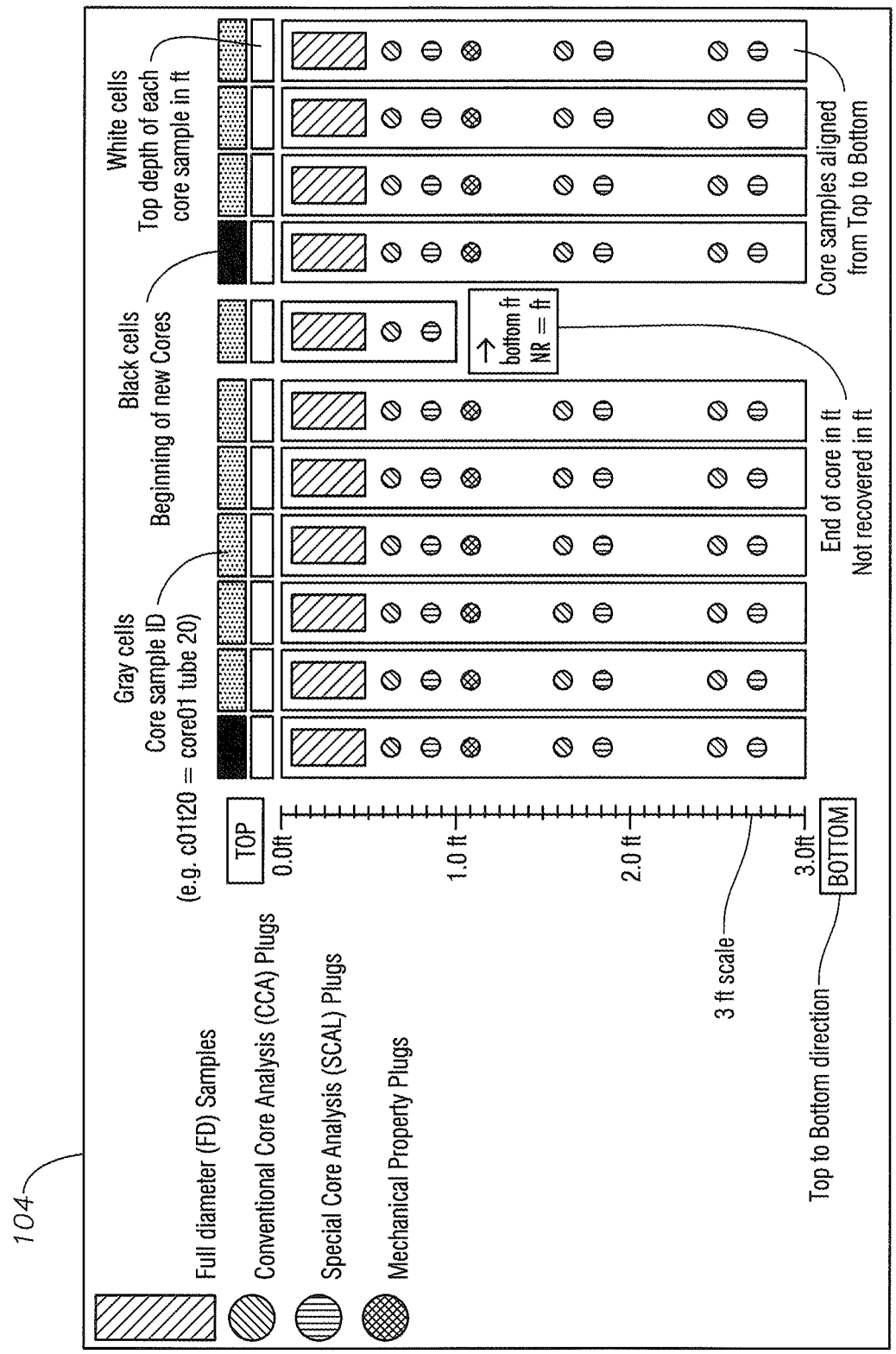
FIG. 23 is a schematic diagram of an electronic user interface according to an embodiment of the disclosure.
Figure 24:
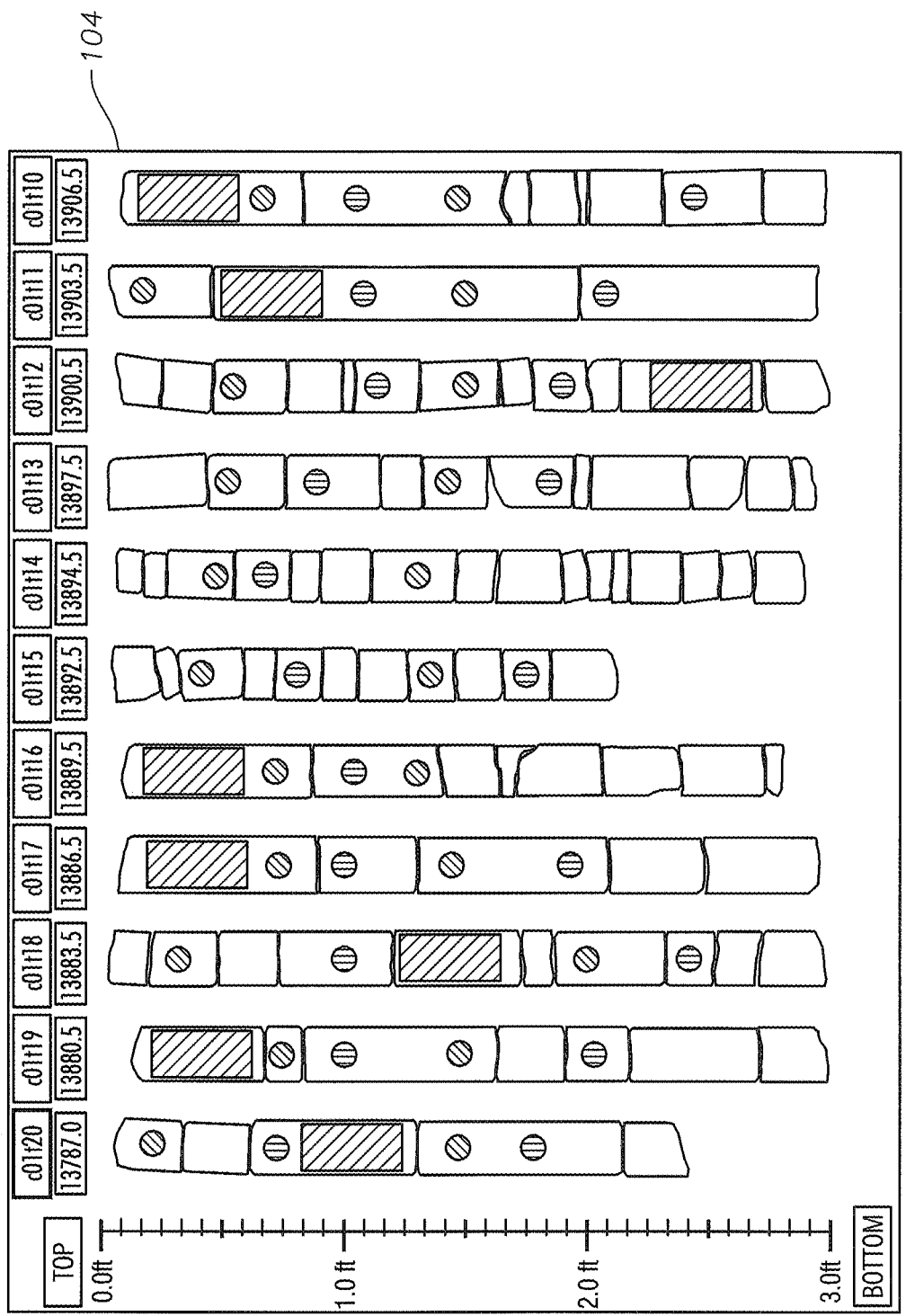
FIG. 24 is a schematic diagram of an electronic user interface according to an embodiment of the disclosure.
Figure 26:
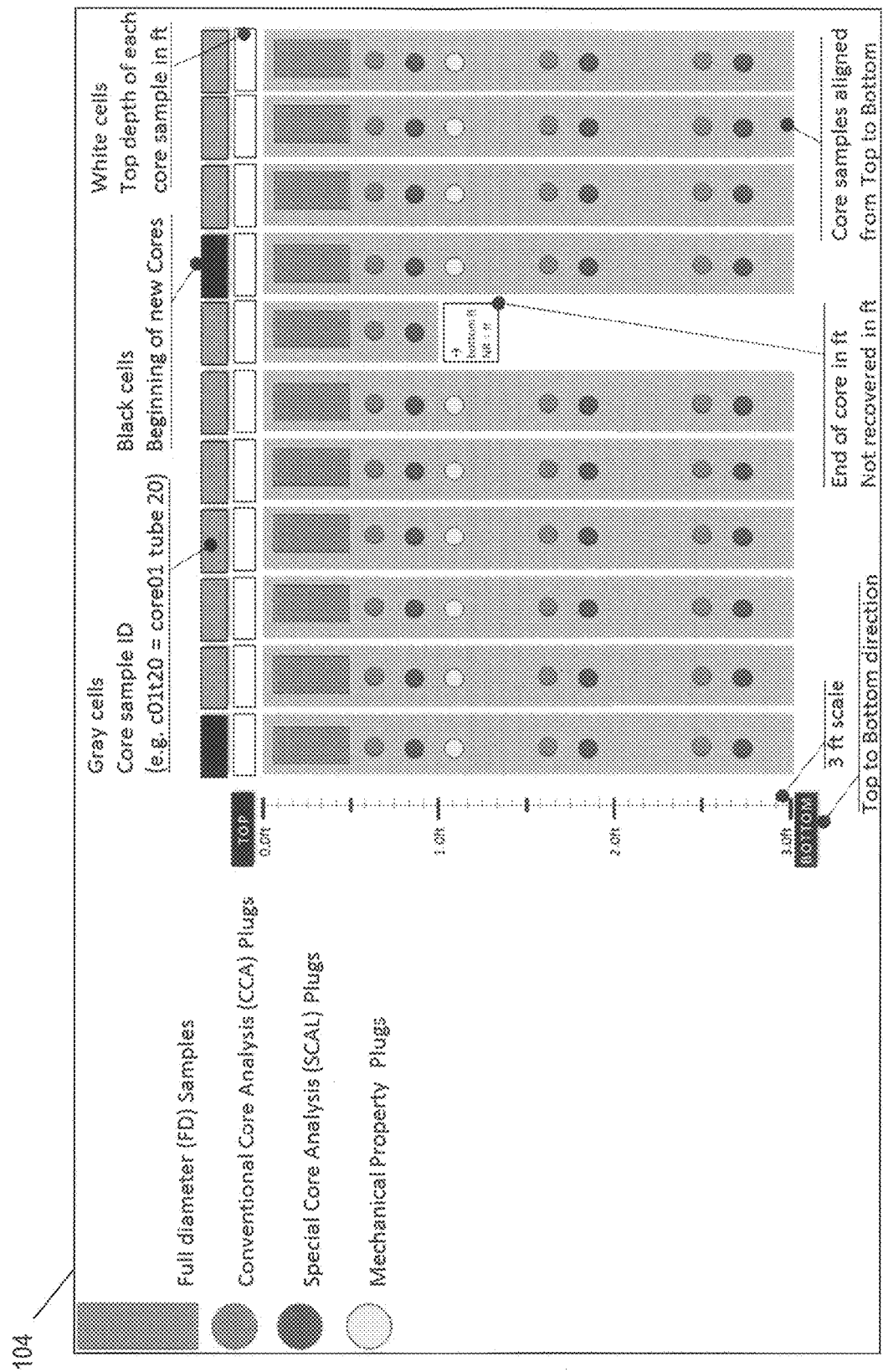
FIG. 26 is a schematic diagram of an electronic user interface according to an embodiment of the disclosure.
Figure 27:
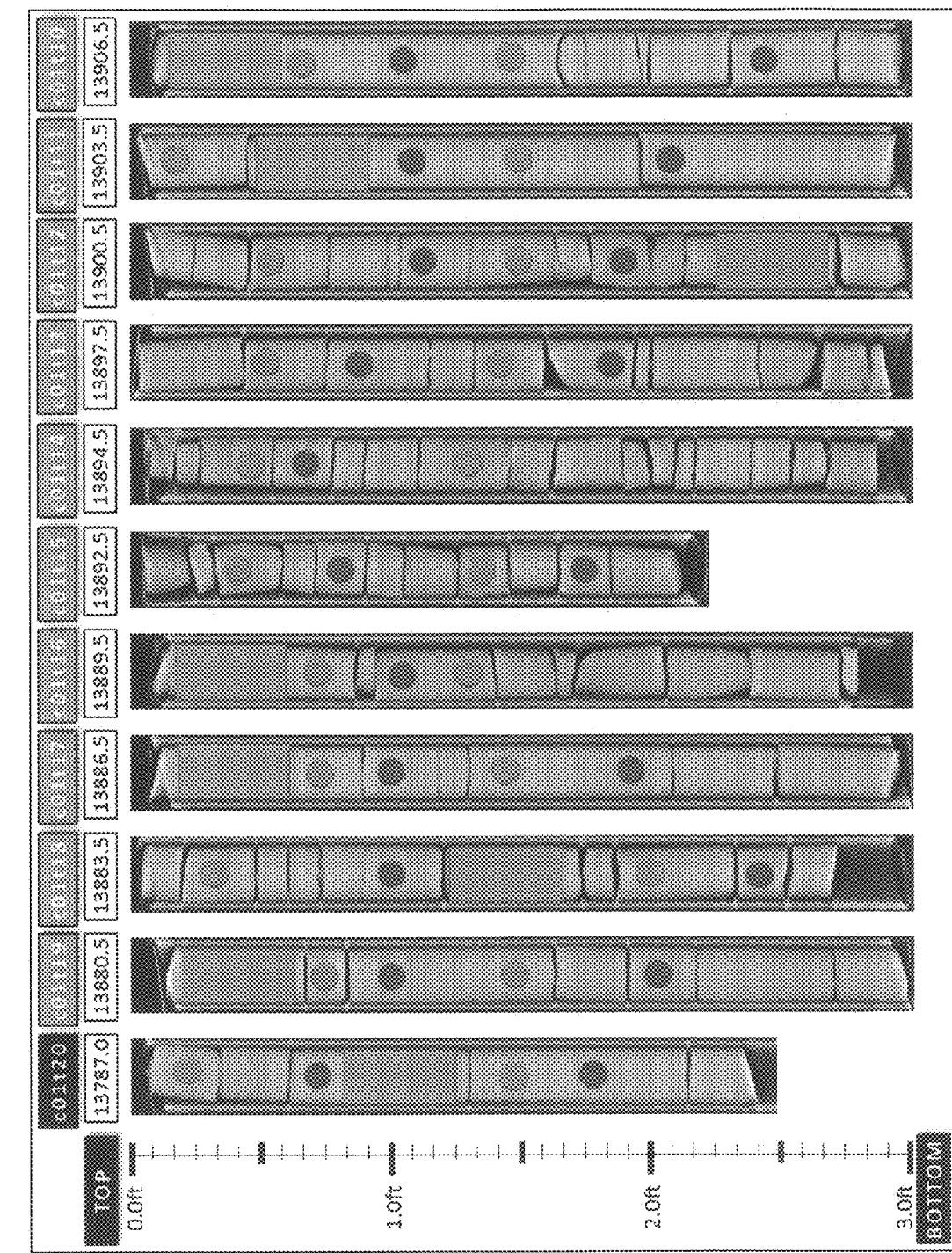
FIG. 27 is a schematic diagram of an electronic user interface according to an embodiment of the disclosure.

In some instances, displaying the plurality of pilot images 215 in a substantially side-by-side arrangement and virtually marking each of the plurality of pilot images 215 can include a series of steps or stages, as illustrated, for example, in FIG. 18, FIG. 19, FIG. 20, FIG. 21, FIG. 22, FIG. 23, FIG. 24, FIG. 26, and FIG. 27. For example, a first step can include transferring one or more dicom images from a CT scanner 102 control unit to a workstation that has image processing capabilities, as will be understood by those skilled in the art. Example dicom image files as depicted on an electronic user interface 104 are illustrated in FIG. 18, for example. Then, pilot image 215 files can be obtained using image processing software that is capable of reading dicom files, as will be understood by those skilled in the art. During this stage (that is, obtaining pilot image 215 files), a unique name that describes an image identification can be assigned to individual pilot images 215. Example tiff image files (after performing processing and naming conventions), as depicted on an electronic user interface 104, are illustrated in FIG. 19, for example. Further, additional example tiff image files (after performing processing and naming conventions), as depicted on an electronic user interface 104, are illustrated in FIG. 20, for example. Additional processing of the final shapes of the pilot images 215 then can be performed. For example, example processed tiff image files (prior to transfer into an advanced core analysis planning format), as depicted on an electronic user interface 104, are illustrated in FIG. 21, for example. Individual images then can be transferred and organized one by one to prepare a format employed in the advanced core analysis planning process that includes the integration of actual depth values for each core sample (that is, drillers depth), as will be understood by those skilled in the art. An advanced core analysis planning format with comprehensive supporting tools, as depicted on an electronic user interface 104, is illustrated in FIG. 22, for example. In addition, advanced core analysis planning marking (that is, virtual marking) can be performed on the advanced core analysis planning format. For example, definitions of terminology and notations in an advanced core analysis planning format, as depicted on an electronic user interface 104, are illustrated in FIG. 23 and FIG. 26, for example. Further, an example methodology of marking the locations of samples in an advanced core analysis planning format, as depicted on an electronic user interface 104, is illustrated in FIG. 23 and FIG. 26, for example. Additionally, markings indicating the locations of samples in an advanced core analysis planning format, as depicted on an electronic user interface 104, are illustrated in FIG. 24 and FIG. 27, for example.

Figure 13:
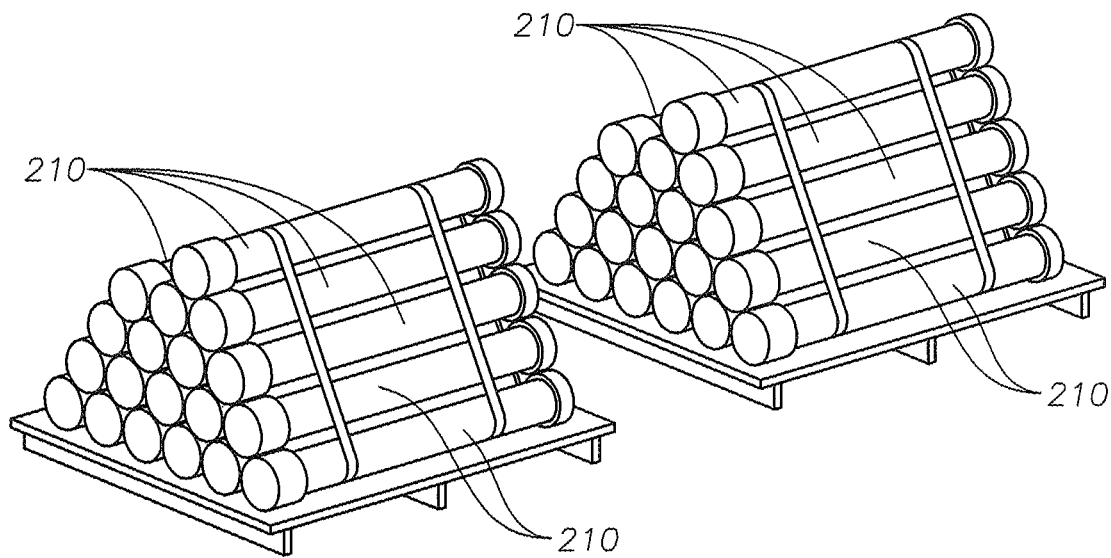
FIG. 13 is a schematic diagram of core samples and containers according to an embodiment of the disclosure.

Advantageously, embodiments of the disclosure can process a large number of core samples 201 encased in containers 210, for example, as illustrated in FIG. 13. Further, the CT scanning techniques of embodiments of the disclosure can significantly contribute to core analysis planning, particularly during the decision-making stage by speeding up the analysis process and increasing the accuracy of the accumulated number of core samples 201 and their locations. Observing the state of core samples 201 using CT scanning images 215 while the core samples 201 are still in their protective core barrels 210 can enable an advanced core analysis planning.

Figure 1:
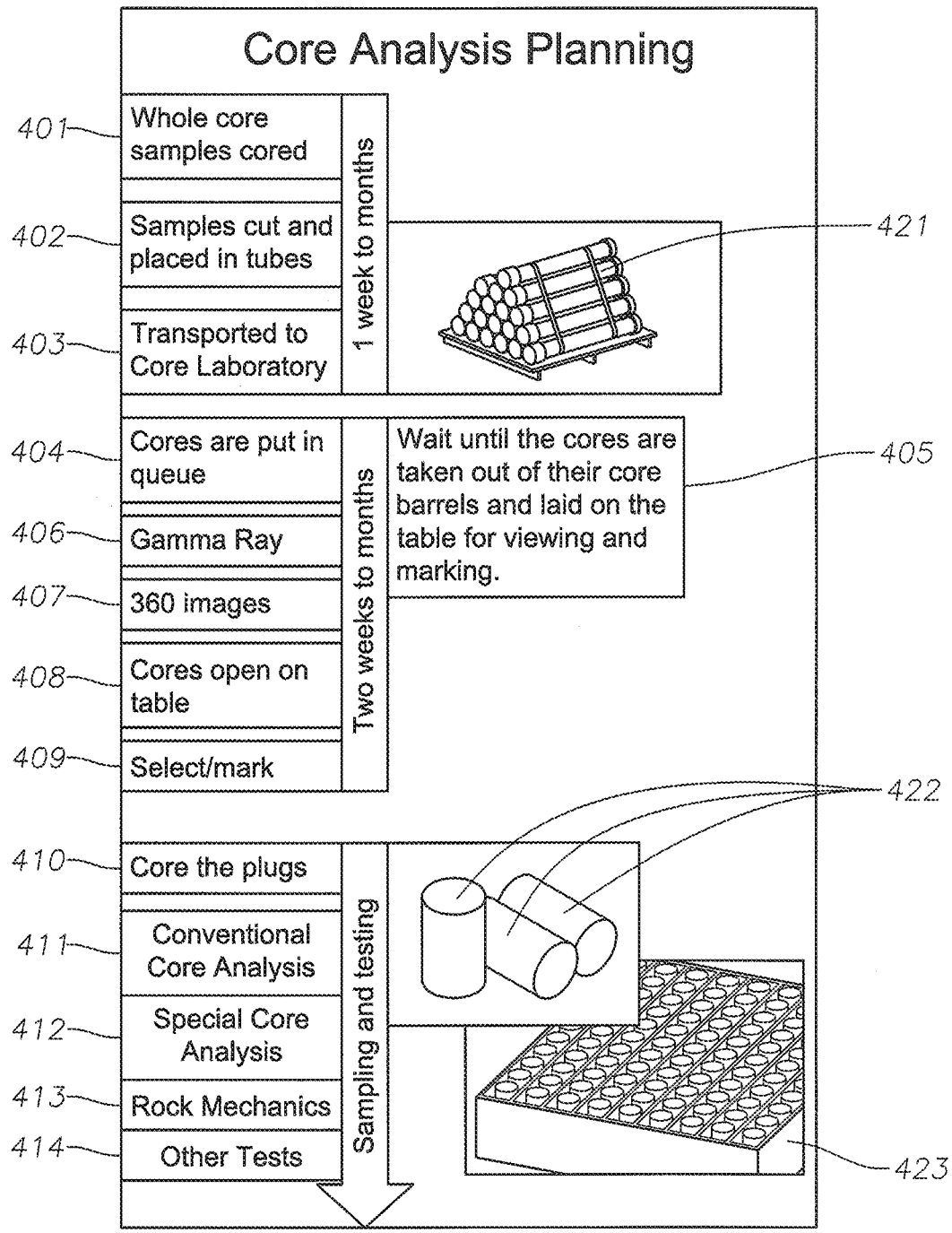
FIG. 1 is a schematic diagram of a method according to the prior art.
Figure 2:
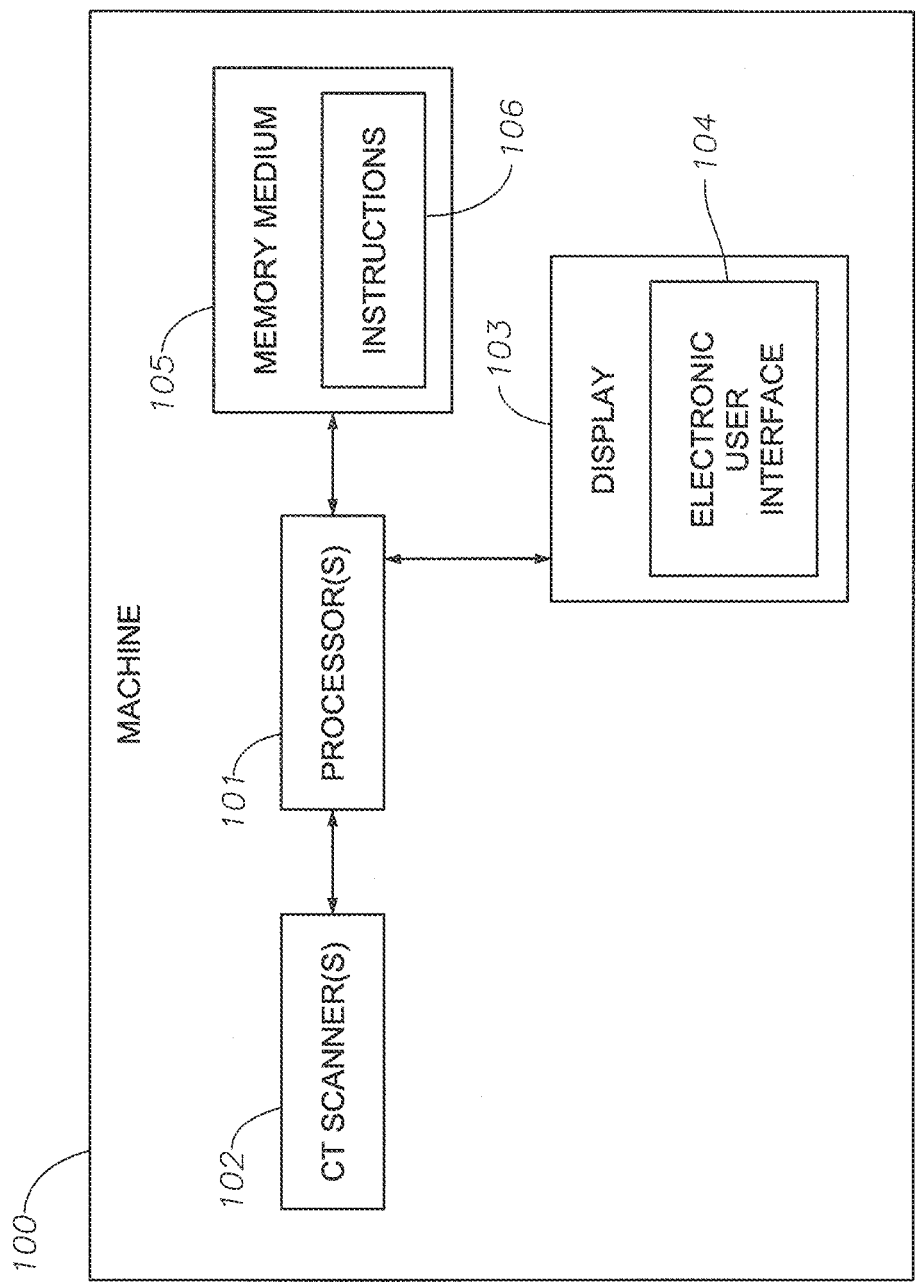
FIG. 2 is a schematic diagram of a system according to an embodiment of the disclosure.

In addition to methods, an embodiment of the disclosure also can include a machine to enhance core analysis planning for core samples of subsurface material. For example, a machine 100 according to an embodiment can include one or more processors 101 and one or more displays 103 in communication with the one or more processors 101, as illustrated in FIG. 2, for example. The one or more displays 103 can be configured to display an electronic user interface 104 on the one or more displays 103, for example. Further, the electronic user interface 104 can have an upper end 141, a lower end 142, a left side 143, and a right side 144, for example, as illustrated in FIG. 5. A machine 100 further can include non-transitory memory medium 105 in communication with the one or more processors 101. The memory medium 105 can include computer-readable instructions 106 stored in the memory medium 105 that, when executed, cause the one or more processors 101 to perform a series of operations. For example, the operations can include positioning a plurality of electronic, two-dimensional, substantially rectangular depictions 215 of structure of one or more real, three-dimensional, substantially cylindrical core samples 201 of subsurface material in a substantially side-by-side arrangement on one or more of the one or more displays 103. Each of the one or more core samples 201 can have a first end 202 and a second end 203. Further, the second end 203 of each of the one or more core samples 201 can be associated with an original location within a corebore 200 downhole relative to an original location within the corebore 200 of the first end 202 of the respective one of the one or more core samples 201. Each core sample 201 also can be encased in a substantially cylindrical container 210 thereby to define an encased core. The plurality of depictions 215 of structure of the one or more encased cores thereby can define a plurality of pilot images 215, for example. Further, each of the plurality of pilot images 215 can have a first end 215a of the pilot image 215 that is associated with the first end 202 of the respective core sample 201 depicted in the respective pilot image 215 and a second end 215b of the pilot image 215 that is associated with the second end 203 of the respective core sample 201 depicted in the respective pilot image 215. The respective first end 215a of each of the pilot images 215 can be aligned along an imaginary line 149 substantially near the upper end 141 of the electronic user interface 104, for example. The operations also can include determining each of one or more portions of each of the plurality of pilot images 215 as one of a plurality of planned sample types thereby to virtually mark each of the plurality of pilot images 215.

In some instances, the one or more core samples 201 can be a plurality of core samples 201, and the plurality of core samples 201 can have a sequential order associated with original locations by downhole position of the plurality of core samples 201 within the corebore 200. Further, the first end 202 of each of the plurality of core samples 201—other than the first core sample in the sequential order—can be associated with an original location within the corebore 200 downhole relative to an original location within the corebore 200 of the second end 203 of the respective prior core sample in the sequential order. Additionally, the plurality of pilot images 215 can be arranged in an order on the electronic user interface 104 thereby to define a display order, and a position within the display order can be associated with the position within the sequential order of the plurality of core samples 201 of the respective core sample 201 depicted in the respective pilot image 215. The display order also can be one of the following: from the left side 143 to the right side 144 of the electronic user interface 104, from the right side 144 to the left side 143 of the electronic interface 104, from the upper end 141 to the lower end 142 of the electronic user interface 104, and from the lower end 142 to the upper end 141 of the electronic user interface 104. The operations further can include superimposing, on the electronic user interface 104, a geometric shape on each of the one or more portions of each of the plurality of pilot images 215 responsive to the virtual mark of the plurality of pilot images 215. Further, each of the plurality of planned sample types can have a predetermined geometric shape associated therewith, and the respective geometric shape associated with each of the plurality of planned sample types can be depicted as a different color. For example, the plurality of planned sample types can include a full diameter sample, a special core analysis (SCAL) sample, a conventional core analysis (CCA) sample, and a mechanical property sample. Still further, in some circumstances, determining each of the one or more portions of each of the plurality of pilot images 215 as one of the plurality of planned sample types can include simulating a respective position of a planned testing sample on the respective core sample 201 depicted in the respective pilot image 215. The operations further can include displaying, by use of the electronic user interface 104, measurements of depth of the original locations of the plurality of core samples 201 within the corebore 200 and measurements of depth of the original locations of the portions of each of the plurality of core samples 201 associated with each of the one or more virtually marked portions of each of the plurality of pilot images 215.

In addition, in some circumstances, each of the one or more substantially cylindrical containers 210 can be a protective barrier made of one or more of a plurality of materials that are at least partially transparent to electromagnetic energy, and the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). A machine 100 further can include one or more computerized tomography (CT) scanners 102 in communication with the one or more processors 101, as illustrated in FIG. 2, for example. The one or more CT scanners 102 can be configured to scan the one or more encased cores, for example. Additionally, the operations further can include transforming physical properties of the one or more encased cores into the plurality of pilot images 215 responsive to one or more penetrative scans of each of the one or more protective barriers by use of the one or more CT scanners 102, for example.

In addition to machines and methods, an embodiment of the disclosure can include non-transitory computer-readable medium having one or more computer programs stored therein operable by one or more processors to enhance core analysis planning for core samples 201 of subsurface material. For example, in non-transitory computer-readable medium having one or more computer programs stored therein according to an embodiment, the one or more computer programs can include a set of instructions that, when executed by the one or more processors, cause the one or more processors to perform a series of operations. The operations can include, for example, positioning a plurality of electronic, two-dimensional, substantially rectangular depictions 215 of structure of one or more real, three-dimensional, substantially cylindrical core samples 201 of subsurface material in a substantially side-by-side arrangement on a display, for instance. Each of the one or more core samples 201 can have a first end 202 and a second end 203. Further, the second end 203 of each of the one or more core samples 201 can be associated with an original location within a corebore 200 downhole relative to an original location within the corebore 200 of the first end 202 of the respective one of the one or more core samples 201, for example. Each core sample 201 also can be encased in a substantially cylindrical container 210 thereby to define an encased core. Further, the plurality of depictions 215 of structure of the one or more encased cores thereby can define a plurality of pilot images 215. Each of the plurality of pilot images 215 can have a first end 215a of the pilot image 215 that is associated with the first end 202 of the respective core sample 201 depicted in the respective pilot image 215 and a second end 215b of the pilot image 215 that is associated with the second end 203 of the respective core sample 201 depicted in the respective pilot image 215. The respective first end 215a of each of the pilot images 215 can be aligned along an imaginary line 149 substantially near an upper end 141 of an electronic user interface 104, for example. The operations further can include determining each of one or more portions of each of the plurality of pilot images 215 as one of a plurality of planned sample types thereby to virtually mark each of the plurality of pilot images 215.

In some circumstances, the one or more core samples 201 can be a plurality of core samples 201, and the plurality of core samples 201 can have a sequential order associated with original locations by downhole position of the plurality of core samples 201 within the corebore 200. Further, the first end 202 of each of the plurality of core samples 201 (other than the first core sample in the sequential order) can be associated with an original location within the corebore 200 downhole relative to an original location within the corebore 200 of the second end 203 of the respective prior core sample in the sequential order. The plurality of pilot images 215 can be arranged in an order on the electronic user interface 104 thereby to define a display order, and a position within the display order can be associated with the position within the sequential order of the plurality of core samples 201 of the respective core sample 201 depicted in the respective pilot image 215. Further, the display order can be one of the following: from a left side 143 to a right side 144 of the electronic user interface 104, from the right side 144 to the left side 143 of the electronic interface 104, from the upper end 141 to a lower end 142 of the electronic user interface 104, and from the lower end 142 to the upper end 141 of the electronic user interface 104. Additionally, the operations further can include superimposing a geometric shape on each of the one or more portions of each of the plurality of pilot images 215 responsive to the virtual mark of the plurality of pilot images 215. For example, each of the plurality of planned sample types can have a predetermined geometric shape associated therewith, and the respective geometric shape associated with each of the plurality of planned sample types can be depicted as a different color. Further, the plurality of planned sample types can include a full diameter sample, a special core analysis (SCAL) sample, a conventional core analysis (CCA) sample, and a mechanical property sample. In some instances, determining each of the one or more portions of each of the plurality of pilot images 215 as one of the plurality of planned sample types can include simulating a respective position of a planned testing sample on the respective core sample 201 depicted in the respective pilot image 215. Further, the operations also can include displaying measurements of depth of the original locations of the plurality of core samples 201 within the corebore 200 and measurements of depth of the original locations of the portions of each of the plurality of core samples 201 associated with each of the one or more virtually marked portions of each of the plurality of pilot images 215.

In some instances, each of the one or more substantially cylindrical containers 210 can be a protective barrier made of one or more of a plurality of materials that are at least partially transparent to electromagnetic energy, and the plurality of materials can include aluminum, polyvinyl chloride (PVC), cardboard, polyethylene (PE), polypropylene (PP), carbon fiber, fiberglass, polycarbonates, and poly(methyl methacrylate) (PMMA). Further, the operations can include transforming physical properties of the one or more encased cores into the plurality of pilot images 215 responsive to one or more penetrative scans of each of the one or more protective barriers by use of one or more computerized tomography (CT) scanners 102.

Further, for example, a machine 100 according to another embodiment can include one or more processors 101 and one or more computerized tomography (CT) scanners 102 in communication with the one or more processors 101, as illustrated, for example, FIG. 2. An example CT scanner 102 is illustrated in FIG. 14, for example. The one or more CT scanners 102 can be configured to scan a plurality of real, three-dimensional, substantially cylindrical core samples 201 of subsurface material, as illustrated in FIG. 9, for example. Each core sample 201 can be encased in a substantially cylindrical container 210, as illustrated in FIG. 8, for example, and the encased core samples 201 thereby can define a plurality of encased cores. For example, in some instances, the substantially cylindrical container 210 can be a protective barrier made of one or more of the following opaque materials: aluminum, fiberglass, and PVC pipe. Further, each of the plurality of core samples 201 can have a first end 202 and a second end 203, as illustrated in FIG. 9, for example. Additionally, the plurality of core samples 201 can have a sequential order associated with original locations by depth of the plurality of core samples 201 within a corebore 200, for example, as illustrated in FIG. 10. The second end 203 of each of the plurality of core samples 201 can be associated with a deeper original location within the corebore 200 than the first end 202 of the respective one of the plurality of core samples 201. In addition, the first end 202 of each of the plurality of core samples 201—other than the first core sample in the sequential order—can be associated with a deeper original location within the corebore 200 than the second end 203 of the respective prior core sample in the sequential order.

A machine 100 according to another embodiment also can include one or more displays 103 in communication with the one or more processors 101 and configured to display an electronic user interface 104 thereon, as illustrated in FIG. 2, for example. The electronic user interface 104 can have an upper end 141, a lower end 142, a left side 143, and a right side 144, for example, as illustrated in FIG. 5. A machine 100 further can include non-transitory memory medium 105 in communication with the one or more processors 101. The memory medium 105 can include computer-readable instructions 106 stored therein that when executed cause the one or more processors 101 to perform a series of operations. For example, the operations can include transforming physical properties of each of the plurality of encased cores into an electronic, two-dimensional, substantially rectangular depiction of structure of the respective encased core responsive to the one or more CT scanners 102 thereby to define a pilot image 215, as illustrated in FIG. 5, for example. That is, a pilot image 215 can depict both a core sample 201 and its respective container 210. Each of the plurality of pilot images 215 can have a first end 215a of the pilot image 215 that can be associated with the first end 202 of the respective core sample 201 depicted in the respective pilot image 215. Each of the plurality of pilot images 215 also can have a second end 215b of the pilot image 215 that can be associated with the second end 203 of the respective core sample 201 depicted in the respective pilot image.

The operations also can include displaying—by use of the electronic user interface 104—the plurality of pilot images 215 in a substantially side-by-side arrangement in which (1) the respective first end 215a of each of the pilot images 215 is aligned along an imaginary line 149 substantially near the upper end 141 of the electronic user interface 104 and (2) the plurality of pilot images 215 are arranged in an order from the left side 143 to the right side 144 of the electronic user interface 104 thereby to define a display order, as illustrated, for instance, in FIG. 12. In addition, a position within the display order can be associated with the position within the sequential order of the plurality of core samples 201 of the respective core sample 201 depicted in the respective pilot image 215, for example. Furthermore, the operations also can include identifying each of one or more portions of each of the plurality of pilot images 215 as one of a plurality of sample types thereby to virtually mark each of the plurality of pilot images 215.

In some instances, the operations further can include displaying—by use of the electronic user interface 104—a geometric shape superimposed on each of the one or more portions of each of the plurality of pilot images 215 responsive to the virtual mark of the plurality of pilot images 215, as illustrated in FIG. 6, for example. More specifically, each of the plurality of sample types can have a predetermined geometric shape associated therewith. As depicted in FIG. 6, for example, geometric shapes can include rectangles and circles. Further, the respective geometric shape associated with each of the plurality of sample types can be depicted as a different color. In addition, the plurality of sample types can include a full diameter sample, a special core analysis (SCAL) sample, a conventional core analysis (CCA) sample, and a mechanical property sample. Further, in some circumstances, identifying each of the one or more portions of each of the plurality of pilot images 201 as one of the plurality of sample types can include simulating a respective position of a planned testing sample on the respective core sample 201 depicted in the respective pilot image 201, as illustrated in FIG. 6, for example. For instance, a planned testing sample can include a full diameter sample, a SCAL plug, a CCA plug, and a mechanical property plug.

Additionally, the operations further can include displaying, by use of the electronic user interface 104, measurements of depth of the original locations of the plurality of core samples 201 within the corebore 200 and measurements of depth of the original locations of the portions of each of the plurality of core samples 201 associated with each of the one or more virtually marked portions of each of the plurality of pilot images 215, as illustrated in FIG. 7A and FIG. 7B, for example.

A machine 100 further can include, in some instances, one or more gamma ray detecting devices in communication with the one or more processors 101, for example. The one or more gamma ray detecting devices can be configured to detect gamma rays emitted by subsurface material of the plurality of encased cores. In addition, the operations further can include measuring gamma ray emissions for each of the plurality of encased cores responsive to the one or more gamma ray detecting devices. The operations still further can include associating the measured gamma ray emissions for each of the plurality of encased cores with the respective pilot image 215 that depicts the respective core sample 201 of the respective encased core. In addition, in some circumstances, the one or more gamma ray detecting devices can be one or more or more of: gamma ray spectrometers, scintillation detectors, sodium iodide scintillation counters, and high-purity germanium detectors.

In addition to machines, another embodiment of the disclosure also can include a method to enhance core analysis planning for a plurality of core samples of subsurface material. A method according to another embodiment can relate to a plurality of real, three-dimensional, substantially cylindrical core samples 201 of subsurface material. Each core sample 201 can be encased in a substantially cylindrical container 210 such that the plurality of real, three-dimensional, substantially cylindrical core samples 201 of subsurface material as encased thereby define a plurality of encased cores. A method according to another embodiment can include transforming physical properties of each of the plurality of encased cores into an electronic, two-dimensional, substantially rectangular depiction of structure of the respective encased core responsive to one or more computerized tomography (CT) scanners 102 thereby to define a pilot image 215. Further, each of the plurality of core samples 201 can have a first end 202 and a second end 203. Additionally, the plurality of core samples 201 can have a sequential order associated with original locations by depth of the plurality of core samples 201 within a corebore 200. Further, the second end 203 of each of the plurality of core samples 201 can be associated with a deeper original location within the corebore 200 than the first end 202 of the respective one of the plurality of core samples 201. In addition, the first end 202 of each of the plurality of core samples 201—other than the first core sample in the sequential order—can be associated with a deeper original location within the corebore 200 than the second end 203 of the respective prior core sample in the sequential order. Further, each of the plurality of pilot images 215 can have a first end 215a of the pilot image 215 that can be associated with the first end 202 of the respective core sample 201 depicted in the respective pilot image 215 and a second end 215b of the pilot image 215 that can be associated with the second end 203 of the respective core sample 201 depicted in the respective pilot image 215.

A method according to another embodiment also can include displaying the plurality of pilot images 215 in a substantially side-by-side arrangement in which (1) the respective first end 215a of each of the pilot images 215 is aligned along an imaginary line 149 substantially near an upper end 141 of an electronic user interface 104 and (2) the plurality of pilot images 215 are arranged in an order from a left side 143 to a right side 144 of the electronic user interface 104 thereby to define a display order. For example, a position within the display order can be associated with the position within the sequential order of the plurality of core samples 201 of the respective core sample 201 depicted in the respective pilot image 215. A method according to another embodiment further can include identifying each of one or more portions of each of the plurality of pilot images 215 as one of a plurality of sample types thereby to virtually mark each of the plurality of pilot images 215.

In some circumstances, a method according to another embodiment further can include displaying a geometric shape superimposed on each of the one or more portions of each of the plurality of pilot images 215 responsive to the virtual mark of the plurality of pilot images 215. For example, each of the plurality of sample types can have a predetermined geometric shape associated therewith, and the respective geometric shape associated with each of the plurality of sample types can be depicted as a different color. In addition, the plurality of sample types can include a full diameter sample, a special core analysis (SCAL) sample, a conventional core analysis (CCA) sample, and a mechanical property sample. Further, in some instances, identifying each of the one or more portions of each of the plurality of pilot images 215 as one of the plurality of sample types can include simulating a respective position of a planned testing sample on the respective core sample 201 depicted in the respective pilot image 215. Additionally, a method still further can include displaying measurements of depth of the original locations of the plurality of core samples 201 within the corebore 200 and measurements of depth of the original locations of the portions of each of the plurality of core samples 201 associated with each of the one or more virtually marked portions of each of the plurality of pilot images 215.

In addition, in some instances, a method according to another embodiment further can include measuring gamma ray emissions for each of the plurality of encased cores responsive to one or more gamma ray detecting devices. A method also can include associating the measured gamma ray emissions for each of the plurality of encased cores with the respective pilot image 215 that depicts the respective core sample 201 of the respective encased core. Further, the one or more gamma ray detecting devices can be one or more or more of: gamma ray spectrometers, scintillation detectors, sodium iodide scintillation counters, and high-purity germanium detectors. Additionally, the substantially cylindrical container 210 can be a protective barrier made of one or more of the following opaque materials: aluminum, fiberglass, and PVC pipe, in some circumstances.

In addition to machines and methods, another embodiment of the disclosure can include non-transitory computer-readable medium having one or more computer programs stored therein operable by one or more processors to enhance core analysis planning for a plurality of core samples 201 of subsurface material. The one or more computer programs can include a set of instructions that, when executed by the one or more processors, cause the one or more processors to perform a series of operations. For example, the operations can relate to a plurality of real, three-dimensional, substantially cylindrical core samples 201 of subsurface material. Each core sample 201 can be encased in a substantially cylindrical container 210, and the plurality of core samples 201 so encased thereby can define a plurality of encased cores. More specifically, the operations can include transforming physical properties of each of the plurality of encased cores into an electronic, two-dimensional, substantially rectangular depiction of structure of the respective encased core responsive to one or more computerized tomography (CT) scanners 102 thereby to define a pilot image 215. Each of the plurality of core samples 201 can have a first end 202 and a second end 203, and the plurality of core samples 201 can have a sequential order associated with original locations by depth of the plurality of core samples 201 within a corebore 200. Further, the second end 203 of each of the plurality of core samples 201 can be associated with a deeper original location within the corebore 200 than the first end 202 of the respective one of the plurality of core samples 201. In addition, the first end 202 of each of the plurality of core samples 201 (other than the first core sample in the sequential order) can be associated with a deeper original location within the corebore 200 than the second end 203 of the respective prior core sample in the sequential order. Further, each of the plurality of pilot images 215 can have a first end 215a of the pilot image 215 that can be associated with the first end 202 of the respective core sample 201 depicted in the respective pilot image 215 and a second end 215b of the pilot image 215 that can be associated with the second end 203 of the respective core sample 201 depicted in the respective pilot image 215.

The operations also can include displaying the plurality of pilot images 215 in a substantially side-by-side arrangement in which (1) the respective first end 215a of each of the pilot images 215 is aligned along an imaginary line 149 substantially near an upper end 141 of an electronic user interface 104 and (2) the plurality of pilot images 215 are arranged in an order from a left side 143 to a right side 144 of the electronic user interface 104 thereby to define a display order. A position within the display order can be associated with the position within the sequential order of the plurality of core samples 201 of the respective core sample 201 depicted in the respective pilot image 215. The operations further can include identifying each of one or more portions of each of the plurality of pilot images 215 as one of a plurality of sample types thereby to virtually mark each of the plurality of pilot images 215.

In some instances, the operations still further can include displaying a geometric shape superimposed on each of the one or more portions of each of the plurality of pilot images 215 responsive to the virtual mark of the plurality of pilot images 215. Further, each of the plurality of sample types can have a predetermined geometric shape associated therewith, and the respective geometric shape associated with each of the plurality of sample types can be depicted as a different color. Additionally, in some instances, the plurality of sample types can include a full diameter sample, a special core analysis (SCAL) sample, a conventional core analysis (CCA) sample, and a mechanical property sample. Further, identifying each of the one or more portions of each of the plurality of pilot images 215 as one of the plurality of sample types can include simulating a respective position of a planned testing sample on the respective core sample 201 depicted in the respective pilot image 215. The operations also can include displaying measurements of depth of the original locations of the plurality of core samples 201 within the corebore 200 and measurements of depth of the original locations of the portions of each of the plurality of core samples 201 associated with each of the one or more virtually marked portions of each of the plurality of pilot images 215.

Additionally, in some circumstances, the operations further can include measuring gamma ray emissions for each of the plurality of encased cores responsive to one or more gamma ray detecting devices. The operations also can include associating the measured gamma ray emissions for each of the plurality of encased cores with the respective pilot image 215 that depicts the respective core sample 201 of the respective encased core. Further, the one or more gamma ray detecting devices can be one or more or more of: gamma ray spectrometers, scintillation detectors, sodium iodide scintillation counters, and high-purity germanium detectors. In addition, the substantially cylindrical container 210 can be a protective barrier made of one or more of the following opaque materials: aluminum, fiberglass, and PVC pipe, in some instances.

Further, methods, machines, and non-transitory computer-readable medium having one or more computer programs stored therein according to yet another embodiment of the disclosure similarly can include virtually marking images of non-encased core samples 201, as well. For example, a method can include positioning a plurality of electronic, two-dimensional, substantially rectangular depictions of structure of one or more real, three-dimensional, substantially cylindrical core samples 201 of subsurface material in a substantially side-by-side arrangement on a display. Each of the one or more core samples 201 can have a first end 202 and a second end 203, and the second end 203 of each of the one or more core samples 201 can be associated with an original location within a corebore 200 downhole relative to an original location within the corebore 200 of the first end 202 of the respective one of the one or more core samples 201. The plurality of depictions of structure of the one or more core samples 201 thereby can define a plurality of non-encased pilot images. Each of the plurality of non-encased pilot images can have a first end of the non-encased pilot image associated with the first end 202 of the respective core sample 201 depicted in the respective non-encased pilot image and a second end of the non-encased pilot image associated with the second end 203 of the respective core sample 201 depicted in the respective non-encased pilot image. Further, the respective first end of each of the non-encased pilot images can be aligned along an imaginary line substantially near an upper end of an electronic user interface. A method also can include determining each of one or more portions of each of the plurality of non-encased pilot images as one of a plurality of planned sample types thereby to virtually mark each of the plurality of non-encased pilot images. Such a method can include other steps and features similar to those described supra with respect to encased cores and pilot images 215 and can be associated with related machines and non-transitory computer-readable medium having one or more computer programs stored therein. Further, performing such core analysis planning for non-encased cores 201 advantageously can reduce processing time compared to the prior art.

In the various embodiments of the disclosure, a person having ordinary skill in the art will recognize that various types of memory are readable by a computer, such as the memory described in the disclosure in reference to the various computers and servers, for example, computer, computer server, web server, or other computers with embodiments of the present disclosure. Examples of computer-readable media can include but are not limited to: nonvolatile, hard-coded type media, such as read only memories (ROMs), CD-ROMs, and DVD-ROMs, or erasable, electrically programmable read only memories (EEPROMs); recordable type media, such as floppy disks, hard disk drives, CD-R/RWs, DVD-RAMs, DVD-R/RWs, DVD+R/RWs, flash drives, memory sticks, and other newer types of memories; and transmission type media such as digital and analog communication links. For example, such media can include operating instructions, as well as instructions related to the systems and the method steps described supra and can operate on a computer. It will be understood by those skilled in the art that such media can be at other locations instead of, or in addition to, the locations described to store computer program products, for example, including software thereon. It will be understood by those skilled in the art that the various software modules or electronic components described supra can be implemented and maintained by electronic hardware, software, or a combination of the two, and that such embodiments are contemplated by embodiments of the present disclosure.

In the drawings and specification, there have been disclosed embodiments of methods, machines, systems, and non-transitory computer-readable medium having computer program stored therein of the present disclosure, and although specific terms are employed, the terms are used in a descriptive sense only and not for purposes of limitation. The embodiments of methods, machines, systems, and non-transitory computer-readable medium having computer program stored therein of the present disclosure have been described in considerable detail with specific reference to these illustrated embodiments. It will be apparent, however, that various modifications and changes can be made within the spirit and scope of the embodiments of methods, machines, systems, and non-transitory computer-readable medium having computer program stored therein of the present disclosure as described in the foregoing specification, and such modifications and changes are to be considered equivalents and part of this disclosure.

That claimed is:

1. A method to enhance core analysis planning for core samples of subsurface material, the method comprising:
    obtaining a plurality of pilot images corresponding to a respective plurality of electronic, two-dimensional, rectangular depictions of structure of one or more three-dimensional core samples of subsurface material, each of the one or more core samples having a first end and a second end, each of the plurality of pilot images having a first end of the pilot image associated a the first end of the respective core sample depicted in the respective pilot image and a second end of the pilot image associated with the second end of the respective core sample depicted in the respective pilot image, each of the one or more core samples encased in a respective one or more cylindrical containers thereby to define an encased core, wherein each of the one or more cylindrical containers is a protective barrier made of one or more of a plurality of materials that are transparent to X-rays, and wherein the plurality of materials includes aluminum, polyvinyl chloride (PVC), cardboard, polyethylene (PE), polypropylene (PP), carbon fiber, fiberglass, polycarbonates, and poly(methyl methacrylate) (PMMA);
    determining a portion of one the plurality of pilot images as one of a plurality of planned sample types, wherein the plurality of planned sample types include a full diameter sample, a special core analysis (SCAL) sample, a conventional core analysis (CCA) sample, and a mechanical property sample;
    virtually marking one of the plurality of pilot images based on the determination; and
    transforming physical properties of the one or more encased cores into the plurality of pilot images responsive to one or more penetrative scans of the protective barrier by use of one or more computerized tomography (CT) scanners.

2. The method of claim 1, wherein the second end of each of the one or more core samples is associated with an original location within a corebore downhole relative to an original location within the corebore of the first end of the respective one of the one or more core samples.

3. The method of claim 1, wherein the one or more core samples are a plurality of core samples, wherein the plurality of core samples have a sequential order associated with original locations by downhole position of the plurality of core samples within a corebore, wherein the first end of each of the plurality of core samples other than the first core sample in the sequential order is associated with an original location within the corebore downhole relative to an original location within the corebore of the second end of the respective prior core sample in the sequential order.

4. The method of claim 1, wherein the method further comprises superimposing a geometric shape on the portion of one of the plurality of pilot images responsive to the virtual marking, each of the plurality of planned sample types having a predetermined geometric shape associated therewith, the respective geometric shape associated with each of the plurality of planned sample types depicted as a different color.

5. The method of claim 1, wherein determining a portion of one the plurality of pilot images as one of a plurality of planned sample types includes simulating a respective position of a planned testing sample on the respective core sample depicted in the respective pilot image, and wherein the method further comprises displaying measurements of depth of the original locations of the one of the plurality of core samples within a corebore and measurements of depth of an original location of the portion of the one of the plurality of core samples.

6. A machine to enhance core analysis planning for core samples of subsurface material, the machine comprising:
one or more processors;
one or more displays in communication with the one or more processors and configured to display an electronic user interface thereon, the electronic user interface having an upper end, a lower end, a left side, and a right side; and
non-transitory memory medium in communication with the one or more processors, the memory medium including computer-readable instructions stored therein that when executed cause the one or more processors to perform the operations of:
obtaining a plurality of pilot images corresponding to a respective plurality of electronic, two-dimensional, rectangular depictions of structure of one or more core samples of subsurface material, each of the one or more three-dimensional core samples having a first end and a second end, each of the plurality of pilot images having a first end of the pilot image associated a the first end of the respective core sample depicted in the respective pilot image and a second end of the pilot image associated with the second end of the respective core sample depicted in the respective pilot image, each of the one or more core samples encased in a respective one or more cylindrical containers thereby to define one or more encased cores, wherein each of the one or more cylindrical containers is a protective barrier made of one or more of a plurality of materials that are transparent to X-rays, wherein the one or more of plurality of materials comprise aluminum, polyvinyl chloride (PVC), cardboard, polyethylene (PE), polypropylene (PP), carbon fiber, fiberglass, polycarbonates, and poly (methyl methacrylate) (PMMA);
determining a portion of one the plurality of pilot images as one of a plurality of planned sample types, wherein the plurality of planned sample types include a full diameter sample, a special core analysis (SCAL) sample, a conventional core analysis (CCA) sample, and a mechanical property sample; and
virtually marking one of the plurality of pilot images based on the determination; one or more computerized tomography (CT) scanners in communication with the one or more processors and configured to scan the one or more encased cores; and
transforming physical properties of the one or more encased cores into the plurality of pilot images responsive to one or more penetrative scans of the protective barrier by use of one or more computerized tomography (CT) scanners.

7. The machine of claim 6, wherein the second end of each of the one or more core samples is associated with an original location within a corebore downhole relative to an original location within the corebore of the first end of the respective one of the one or more core samples.

8. The machine of claim 6, wherein the one or more core samples are a plurality of core samples, wherein the plurality of core samples have a sequential order associated with original locations by downhole position of the plurality of core samples within a corebore, wherein the first end of each of the plurality of core samples other than the first core sample in the sequential order is associated with an original location within the corebore downhole relative to an original location within the corebore of the second end of the respective prior core sample in the sequential order.

9. The machine of claim 6, wherein the operations further include superimposing a geometric shape on the portion of one of the plurality of pilot images responsive to the virtual marking, each of the plurality of planned sample types having a predetermined geometric shape associated therewith, the respective geometric shape associated with each of the plurality of planned sample types depicted as a different color.

10. The machine of claim 6, wherein determining a portion of one the plurality of pilot images as one of a plurality of planned sample types includes simulating a respective position of a planned testing sample on the respective core sample depicted in the respective pilot image, and wherein the method further comprises displaying measurements of depth of the original locations of the one of the plurality of core samples within a corebore and measurements of depth of an original location of the portion of the one of the plurality of core samples.

11. Non-transitory computer-readable medium having one or more computer programs stored therein operable by one or more processors to enhance core analysis planning for core samples of subsurface material, the one or more computer programs comprising a set of instructions that, when executed by the one or more processors, cause the one or more processors to perform the operations of:
obtaining a plurality of pilot images corresponding to a respective plurality of electronic, two-dimensional, rectangular depictions of structure of one or more three-dimensional core samples of subsurface material, each of the one or more core samples having a first end and a second end, each of the plurality of pilot images having a first end of the pilot image associated a the first end of the respective core sample depicted in the respective pilot image and a second end of the pilot image associated with the second end of the respective core sample depicted in the respective pilot image, each of the one or more core samples encased in a respective one or more cylindrical containers thereby to define one or more encased cores, wherein each of the one or more cylindrical containers is a protective barrier made of one or more of a plurality of materials that are transparent to X-rays, wherein the one or more of plurality of materials comprise aluminum, polyvinyl chloride (PVC), cardboard, polyethylene (PE), polypropylene (PP), carbon fiber, fiberglass, polycarbonates, and poly (methyl methacrylate) (PMMA);
determining a portion of one the plurality of pilot images as one of a plurality of planned sample types, wherein the plurality of planned sample types include a full diameter sample, a special core analysis (SCAL) sample, a conventional core analysis (CCA) sample, and a mechanical property sample;

virtually marking one of the plurality of pilot images based on the determination; and transforming physical properties of the one or more encased cores into the plurality of pilot images responsive to one or more penetrative scans of the protective barrier by use of one or more computerized tomography (CT) scanners.

12. The non-transitory computer-readable medium of claim 11, wherein the second end of each of the one or more core samples is associated with an original location within a corebore downhole relative to an original location within the corebore of the first end of the respective one of the one or more core samples.

13. The non-transitory computer-readable medium of claim 11, wherein the one or more core samples are a plurality of core samples, wherein the plurality of core samples have a sequential order associated with original locations by downhole position of the plurality of core samples within a corebore, wherein the first end of each of the plurality of core samples other than the first core sample in the sequential order is associated with an original location within the corebore downhole relative to an original location within the corebore of the second end of the respective prior core sample in the sequential order.

14. The non-transitory computer-readable medium of claim 11, superimposing a geometric shape on the portion of the one of the plurality of pilot images responsive to the virtual marking, each of the plurality of planned sample types having a predetermined geometric shape associated therewith, the respective geometric shape associated with each of the plurality of planned sample types depicted as a different color.

15. The non-transitory computer-readable medium of claim 11, wherein determining a portion of one the plurality of pilot images as one of a plurality of planned sample types includes simulating a respective position of a planned testing sample on the respective core sample depicted in the respective pilot image, and wherein the method further comprises displaying measurements of depth of the original locations of the one of the plurality of core samples within a corebore and measurements of depth of an original location of the portion of the one of the plurality of core samples.

* * * * *